(12) United States Patent
Kobayashi et al.

(10) Patent No.: US 10,087,421 B2
(45) Date of Patent: Oct. 2, 2018

(54) STEM CELL SUSPENSION

(75) Inventors: Eiji Kobayashi, Tokushima (JP);
Tamaki Wada, Tokushima (JP);
Yasutaka Fujita, Tokushima (JP);
Norihiro Yoshinaga, Tokyo (JP);
Masako Doi, Tokushima (JP); Yasuhiro Fujimoto, Kyoto (JP); Takumi Teratani, Tochigi (JP)

(73) Assignees: OTSUKA PHARMACEUTICAL FACTORY, INC., Tokushima (JP);
JICHI MEDICAL UNIVERSITY, Tochigi (JP)

( * ) Notice: Subject to any disclaimer, the term of this patent is extended or adjusted under 35 U.S.C. 154(b) by 0 days.

(21) Appl. No.: 13/883,371

(22) PCT Filed: Nov. 9, 2011

(86) PCT No.: PCT/JP2011/075843
§ 371 (c)(1),
(2), (4) Date: Jun. 14, 2013

(87) PCT Pub. No.: WO2012/063870
PCT Pub. Date: May 18, 2012

(65) Prior Publication Data
US 2013/0260461 A1    Oct. 3, 2013

(30) Foreign Application Priority Data

Nov. 9, 2010 (JP) .................................. 2010-251273
Dec. 28, 2010 (JP) .................................. 2010-293908

(51) Int. Cl.
| | | |
|---|---|---|
| C12N 5/071 | (2010.01) | |
| C07H 3/04 | (2006.01) | |
| C12N 5/0775 | (2010.01) | |
| A01N 1/02 | (2006.01) | |
| A61K 9/00 | (2006.01) | |
| A61K 47/26 | (2006.01) | |
| A61K 47/36 | (2006.01) | |
| A61K 35/28 | (2015.01) | |
| C08B 31/04 | (2006.01) | |
| C08B 37/02 | (2006.01) | |

(52) U.S. Cl.
CPC ......... *C12N 5/0667* (2013.01); *A01N 1/0226* (2013.01); *A61K 9/0019* (2013.01); *A61K 35/28* (2013.01); *A61K 47/26* (2013.01); *A61K 47/36* (2013.01); *C07H 3/04* (2013.01); *C08B 31/04* (2013.01); *C08B 37/0021* (2013.01); *C12N 5/0663* (2013.01); *C12N 2500/34* (2013.01)

(58) Field of Classification Search
None
See application file for complete search history.

(56) References Cited

U.S. PATENT DOCUMENTS

| | | | | |
|---|---|---|---|---|
| 5,004,681 | A * | 4/1991 | Boyse | C12N 5/0647 424/529 |
| 2005/0048460 | A1* | 3/2005 | Crowe | C12N 9/96 435/2 |
| 2005/0163750 | A1* | 7/2005 | Roser | A61K 9/0019 424/85.2 |
| 2006/0009469 | A1 | 1/2006 | Witchey-Lakshmanan | |
| 2006/0148074 | A1* | 7/2006 | Gorfien | C07K 14/61 435/325 |
| 2006/0257842 | A1 | 11/2006 | Pettegrew | |
| 2007/0190042 | A1 | 8/2007 | Edinger et al. | |
| 2010/0035327 | A1 | 2/2010 | Steele | |
| 2010/0047213 | A1* | 2/2010 | Zeitlin et al. | 424/93.7 |
| 2010/0291679 | A1 | 11/2010 | Edinger et al. | |

FOREIGN PATENT DOCUMENTS

| | | | |
|---|---|---|---|
| JP | 11-004682 | 1/1999 | |
| JP | 3253131 | 2/2002 | |
| JP | 2009-521931 | 6/2009 | |
| JP | 2009-296889 | 12/2009 | |
| WO | 2007/043698 | 4/2007 | |
| WO | 2009115581 A2 | 9/2009 | |
| WO | WO 2010048628 A1 * | 4/2010 | ........... A61K 31/198 |
| WO | 2010057107 A1 | 5/2010 | |

OTHER PUBLICATIONS

Stiff et al. "Autologous bone marrow transplantation using unfractionated cells cryopreserved in dimethylsulfoxide and hydroxyethyl starch without controlled-rate freezing", Blood 70: 974-78, 1987.*
Search report from International Application No. PCT/JP2011/075843, dated Feb. 7, 2012.
New Zealand Further Examination Report dated Mar. 14, 2014.
Dang et al., "Controlled, Scalable Embryonic Stem Cell Differentiation Culture", Stem Cells Rapid Communication, pp. 275-282.
Hidemi Hattori et al., "Preservation of stem cells during cold storage", 43rd Conference of the Japan Society of Medical Electronics & Biological Engineering (May 2004).
Fengshi Chen et al., "Development of New Organ Preservation Solutions in Kyoto University", Yonsei Medical Journal, vol. 45, No. 6, pp. 1107-1114, 2004.

(Continued)

*Primary Examiner* — Emily A Cordas
(74) *Attorney, Agent, or Firm* — Greenblum & Bernstein P.L.C.

(57) ABSTRACT

The present invention provides a mammalian stem cell suspension containing mammalian stem cells and at least one polysaccharide such as trehalose, and the like; a mammalian stem cell aggregation inhibitor containing polysaccharide such as trehalose, and the like; a method of suppressing aggregation of mammalian stem cells, containing suspending the mammalian stem cells in an aqueous physiological solution containing polysaccharide; an inhibitor of a decrease in the survival rate of mammalian stem cells containing polysaccharide such as trehalose and the like; a method of suppressing a decrease in the survival rate of mammalian stem cells, containing suspending the mammalian stem cells in an aqueous physiological solution containing polysaccharides, and the like.

8 Claims, 5 Drawing Sheets

(56) References Cited

OTHER PUBLICATIONS

Shao-Zhi Zhang et al., "Preliminary Study on the Freeze-Drying of Human Bone Marrow-Derived Mesenchymal Stem Cells," Journal of Zhejiang University Science B, vol. 11, No. 11, Nov. 1, 2010, pp. 889-894.
Sasnoor Lalita et al., "Prevention of Apoptosis as a Possible Mechanism Behind Improved Cryoprotection of Hematopoietic Cells by Catalase and Trehalose," Transplanation (Hagerstown), vol. 80, No. 9, Nov. 2005, pp. 1251-1260.
Extended European Search Report From Application No. 11839155.6, dated Mar. 28, 2014.
Office Action From Chinese Patent Application 201180064550.4, dated Apr. 3, 2014.
Eun-Ho Hwang et al., "Effects of Hydrodynamics on Cell Aggregation of CHO-DG44 Cells in Suspension Culture"; The Korean Society for Biotechnology and Bioengineering, 2008 Fall Conference and International Symposium; Oct. 2008; pp. 453.
"Avoiding Cell Clumping of Insect Cultures"; SAFC Biosciences; Mar. 2006; Page not defined.

* cited by examiner

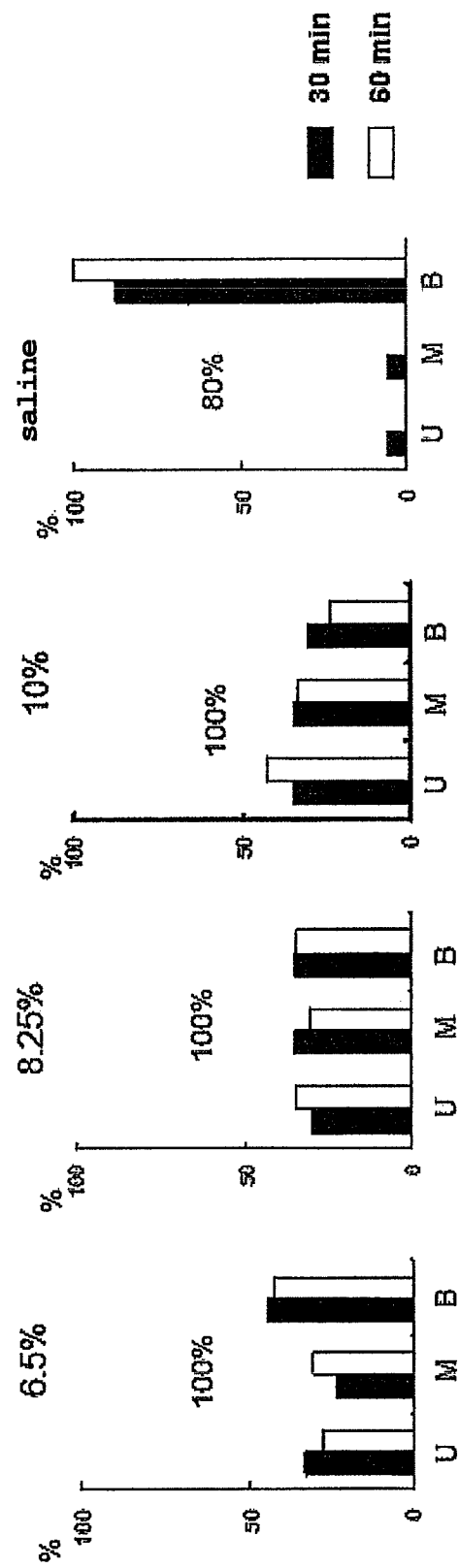

STEM CELL SUSPENSION

TECHNICAL FIELD

The present invention relates to a mammalian stem cell suspension and a pharmaceutical preparation containing it. In addition, the present invention relates to an agent for suppressing aggregation of mammalian stem cells and a method of suppressing aggregation of mammalian stem cells. Furthermore, the present invention relates to an agent for suppressing a decrease in the survival rate of mammalian stem cells, and a method of suppressing a decrease in the survival rate of mammalian stem cells.

BACKGROUND ART

By the advancements in the stem cell research in recent years, clinical application of stem cell has already shifted from the fundamental research stages to the developmental stages. In the treatment of diseases with stem cells, the damaged functions of cells and tissues of the patients are supplemented by said cells and organs newly differentiated from the stem cells. Here, the treatment with stem cells can be largely divided into two according to the manner of differentiation of the stem cells into somatic cells or tissues.

One of them includes in vitro culture of stem cells under particular conditions to allow differentiation into desired somatic cells or tissues, and transplantation of the obtained somatic cells or tissues into the body of a recipient. For example, since pluripotent stem cells such as ES cells, iPS cells and the like are feared to form teratoma when directly transplanted to the body, they are generally differentiated into particular somatic cells or tissues in vitro to certainly eliminate the teratoma forming ability and then transplanted into the body.

The other embodiment includes direct transfer of stem cells into the body. This method has been reported to show effects on diseases such as amyotrophic lateral sclerosis, aplastic anemia, Parkinson's disease, multiple sclerosis, collagen disease, Crohn's disease, ulcerative colitis, Alzheimer's disease, leukemia, lifestyle-related diseases, cancer and the like.

Mesenchymal stem cells are known as stem cells that are present in the bone marrow and the like of mammals, and differentiate into adipocytes, chondrocytes, osteocytes and the like. Due to their multipotency, mesenchymal stem cells are drawing attention as a transplantation material for the regenerative therapy of many tissues. That is, a "regenerative therapy by cell transplantation", which regenerates tissues lost by diseases and disorders, which could not be regenerated by the conventional treatment methods, by using mesenchymal stem cells and recovers the function. Specifically, for example, treatments such as transplantation of bone marrow mesenchymal stem cells to patients with lower leg ischemia (Buerger's disease), transplantation of bone marrow mesenchymal stem cells to the parts affected by periodontal diseases, transplantation of bone marrow mesenchymal stem cells to patients with osteoarthritis and the like have been started or planned.

Trehalose is one kind of disaccharide produced by 1,1-glycosidic linkage of glucoses. Since trehalose imparts sweetness and has high water-holding capacity, it is used for various foods and cosmetics. Moreover, since trehalose stabilizes cellular membranes and suppresses cell injury, it is used as an active ingredient of an organ protection liquid for organ transplantation. There have been developed superior organ preservation solutions containing trehalose such as ET-Kyoto solution, New ET-Kyoto solution and the like (patent documents 1 and 2, non-patent document 1).

Hydroxyethylstarch is one of etherified starches, and used as an adhesive, an emulsifier, a paste and the like.

Dextran is one kind of polysaccharides made from glucose, and widely used as a thickener, a moisturizer and the like in the fields of pharmaceutical products and cosmetics.

DOCUMENT LIST

Patent Documents patent document 1: JP-B-3253131
patent document 2: WO2007/043698

Non-Patent Document non-patent document 1: Yonsei Medical Journal, vol. 45, No. 6, p. 1107-1114, 2004

SUMMARY OF THE INVENTION

Problems to be Solved by the Invention

The present inventors have conducted intensive studies of the conditions for more stably and smoothly performing transplantation of stem cells to the body. They have found that transfer of stem cells into the body, which is, in many cases, performed by drip infusion of a stem cell suspension into the body, may cause, during dripping, aggregation of stem cells in the suspension in an infusion bag to plug the cannula, and form emboli in thin blood vessels such as pulmonary vein and the like. Furthermore, the present inventors have found that the survival rate of the stem cells in an infusion bag may gradually decrease during dripping.

The present invention aims to provide a technique for suppressing aggregation of stem cells in a suspension during transplantation of the stem cells.

In addition, the present invention aims to provide a technique for suppressing a decrease in the survival rate of the stem cells in a suspension.

Means of Solving the Problems

As a result of the intensive studies, the present inventors have found that aggregation of stem cells can be suppressed by adding polysaccharides such as trehalose and the like to a stem cell suspension. In addition, they have also found that such polysaccharides can suppress a decrease in the survival rate of the stem cells. Furthermore, they have also found that the suppressive effect on a decrease in the survival rate of the stem cells can be enhanced by a combination of some of the polysaccharides. Based on these findings, they have conducted further studies and completed the present invention.

That is, the present invention relates to the following.
[1] A mammalian stem cell suspension comprising mammalian stem cells and at least one polysaccharide selected from the group consisting of trehalose, hydroxyethylstarch and dextran.
[2] The mammalian stem cell suspension of [1], comprising a combination comprising trehalose and hydroxyethylstarch, or trehalose and dextran.
[3] The mammalian stem cell suspension of [1], wherein the stem cells are adhesive stem cells.
[4] The mammalian stem cell suspension of [3], wherein the adhesive stem cells are mesenchymal stem cells or pluripotent stem cells.

[5] The mammalian stem cell suspension of [1], wherein the mammalian stem cells comprise mammalian stem cells in a single-cell state.

[6] The mammalian stem cell suspension of [1], wherein the polysaccharide is trehalose having a concentration within the range of 4.53-362.4 mg/ml.

[7] The mammalian stem cell suspension of [1], wherein the polysaccharide is dextran having a concentration within the range of 30-100 mg/ml.

[8] A method of producing a mammalian stem cell suspension, comprising suspending mammalian stem cells in an aqueous physiological solution containing at least one polysaccharide selected from the group consisting of trehalose, hydroxyethylstarch and dextran.

[9] The production method of [8], wherein the aqueous physiological solution comprises trehalose and hydroxyethylstarch, or trehalose and dextran.

[10] A mammalian stem cell suspension preparation comprising the mammalian stem cell suspension of any of [1]-[7].

[11] A mammalian stem cell aggregation inhibitor comprising at least one polysaccharide selected from the group consisting of trehalose, hydroxyethylstarch and dextran.

[12] The mammalian stem cell aggregation inhibitor of [11], wherein the stem cell is an adhesive stem cell.

[13] The mammalian stem cell aggregation inhibitor of [12], wherein the adhesive stem cell is a mesenchymal stem cell or a pluripotent stem cell.

[14] The mammalian stem cell aggregation inhibitor of [11], wherein the polysaccharide is trehalose, which inhibitor is used such that the concentration of trehalose in a mammalian stem cell suspension is within the range of 4.53-362.4 mg/ml.

[15] The mammalian stem cell aggregation inhibitor of [11], wherein the polysaccharide is dextran, which inhibitor is used such that the concentration of dextran is within the range of 30-100 mg/ml.

[16] A method of suppressing aggregation of mammalian stem cells, comprising suspending the mammalian stem cells in an aqueous physiological solution containing at least one polysaccharide selected from the group consisting of trehalose, hydroxyethylstarch and dextran.

[17] The method of suppressing aggregation of mammalian stem cells of [16], wherein the stem cells are adhesive stem cells.

[18] The method of suppressing aggregation of mammalian stem cells of [17], wherein the adhesive stem cells are mesenchymal stem cells or pluripotent stem cells.

[19] The method of suppressing aggregation of mammalian stem cells of [16], wherein the mammalian stem cells comprise mammalian stem cells in a single-cell state.

[20] The method of suppressing aggregation of mammalian stem cells of [16], wherein the polysaccharide is trehalose having a concentration within the range of 4.53-362.4 mg/ml.

[21] The method of suppressing aggregation of mammalian stem cells of [16], wherein the polysaccharide is dextran having a concentration within the range of 30-100 mg/ml.

[22] An inhibitor of a decrease in the survival rate of mammalian stem cells comprising at least one polysaccharide selected from the group consisting of trehalose, hydroxyethylstarch and dextran.

[23] The inhibitor of a decrease in the survival rate of mammalian stem cells of [22], comprising a combination comprising trehalose and hydroxyethylstarch, or trehalose and dextran.

[24] The inhibitor of a decrease in the survival rate of mammalian stem cells of [22], wherein the stem cells are adhesive stem cells.

[25] The inhibitor of a decrease in the survival rate of mammalian stem cells of [24], wherein the adhesive stem cells are mesenchymal stem cells or pluripotent stem cells.

[26] The inhibitor of a decrease in the survival rate of mammalian stem cells of [22], wherein the polysaccharide is trehalose, which inhibitor is used such that the concentration of trehalose in a mammalian stem cell suspension is within the range of 4.53-362.4 mg/ml.

[27] The inhibitor of a decrease in the survival rate of mammalian stem cells of [22], wherein the polysaccharide is dextran, which inhibitor is used such that the concentration of trehalose in a mammalian stem cell suspension is within the range of 30-100 mg/ml.

[28] A method of suppressing a decrease in the survival rate of mammalian stem cells, comprising suspending the mammalian stem cells in an aqueous physiological solution containing at least one polysaccharide selected from the group consisting of trehalose, hydroxyethylstarch and dextran.

[29] The method of suppressing a decrease in the survival rate of mammalian stem cells of [28], wherein the aqueous physiological solution comprises a combination comprising trehalose and hydroxyethylstarch, or trehalose and dextran.

[30] The method of suppressing a decrease in the survival rate of mammalian stem cells of [28], wherein the stem cells are adhesive stem cells.

[31] The method of suppressing a decrease in the survival rate of mammalian stem cells of [30], wherein the adhesive stem cells are mesenchymal stem cells or pluripotent stem cells.

[32] The method of suppressing a decrease in the survival rate of mammalian stem cells of [28], wherein the mammalian stem cells are in a single-cell state.

[33] The method of suppressing a decrease in the survival rate of mammalian stem cells of [28], wherein the polysaccharide is trehalose having a concentration within the range of 15.1-362.4 mg/ml.

[34] The method of suppressing a decrease in the survival rate of mammalian stem cells of [28], wherein the polysaccharide is dextran having a concentration within the range of 30-100 mg/ml.

Effect of the Invention

Using the present invention, aggregation of stem cells in a suspension can be suppressed during transplantation of the stem cells. As a result, the risk of stem cell aggregates plugging a cannula or forming emboli in thin blood vessels such as pulmonary vein and the like decreases.

Using the present invention, moreover, a decrease in the survival rate of the stem cells in a suspension can be suppressed. As a result, a treatment can be performed using stem cells in a better condition, and therefore, the treatment effect can be expected to be enhanced.

BRIEF DESCRIPTION OF THE DRAWINGS

FIG. 6 shows the number of human adipose tissue-derived mesenchymal stem cells in the upper, middle and lower layers of a tube when preserved in a buffer containing dextran 40 (6.5-10 (w/v) %) or saline, wherein the numerical value in the center of the graph shows the survival rate of the total cells.

DESCRIPTION OF EMBODIMENTS

I. Mammalian Stem Cell Suspension

Figure 1:
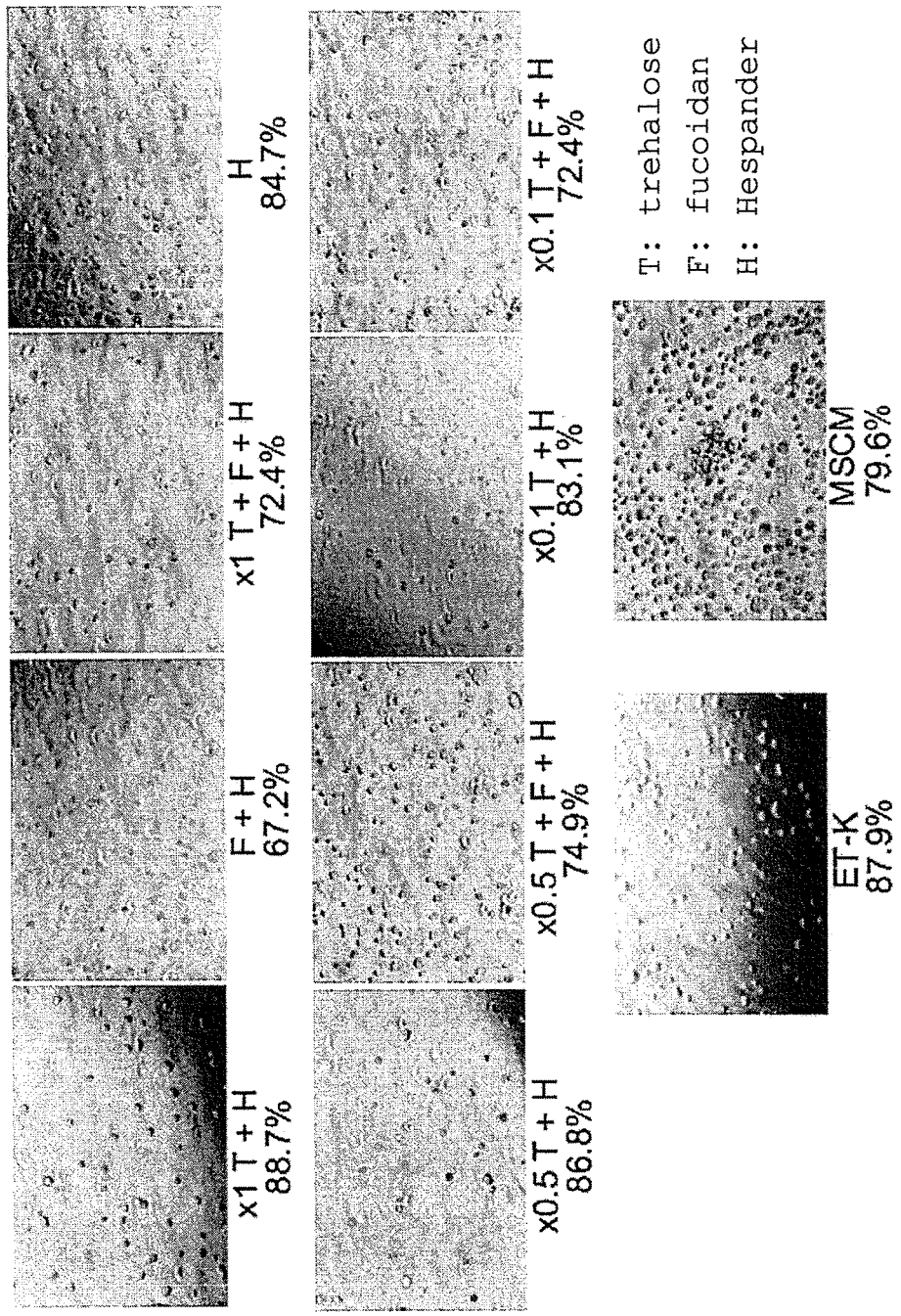
FIG. 1 shows the shape and survival rate of hBM-MSC P6 after standing in each composition solution at 25° C. for 1 hr.

The present invention provides a mammalian stem cell suspension comprising mammalian stem cells and at least one polysaccharide selected from the group consisting of trehalose, hydroxyethylstarch and dextran.

Examples of the mammal include rodents such as mouse, rat, hamster, guinea pig and the like, lagomorpha such as rabbit and the like, ungulata such as swine, bovine, goat, horse, sheep and the like, carnivora such as dog, cat and the like, primates such as human, monkey, *Macaca mulatta*, *Macaca fascicularis*, marmoset, orangutan, chimpanzee and the like, and the like. Mammal is preferably rodent (mouse etc.), ungulate (swine etc.) or primate (human etc.).

In the present specification, the "stem cell" means an immature cell having self replication competence and differentiation/proliferative capacity. The stem cell includes subsets such as pluripotent stem cell, multipotent stem cell, unipotent stem cell and the like, depending on the differentiation capacity. The pluripotent stem cell means a cell that cannot be an individual organism by itself, but has an ability to differentiate into any tissue or cell constituting living organisms. The multipotent stem cell means a cell having an ability to differentiate into plural, though not all, kinds of tissues or cells. The unipotent stem cell means a cell having an ability to differentiate into a particular tissue or cell.

Examples of the pluripotent stem cell include embryonic stem cells (ES cell), EG cell, iPS cell and the like. ES cell can be produced by cultivating an inner cell mass on a feeder cell or in a medium containing LIF. The production methods of ES cell are described in, for example, WO96/22362, WO02/101057, U.S. Pat. No. 5,843,780, U.S. Pat. No. 6,200,806, U.S. Pat. No. 6,280,718 and the like. EG cell can be produced by cultivating a primordial germ cell in a medium containing mSCF, LIF and bFGF (Cell, 70: 841-847, 1992). The iPS cell can be produced by introducing a reprogramming factor such as Oct3/4, Sox2 and Klf4 (further, c-Myc or n-Myc as necessary) and the like into a somatic cell (for example, fibroblast, dermal cell etc.) (Cell, 126: p. 663-676, 2006; Nature, 448: p. 313-317, 2007; Nat Biotechnol, 26: p. 101-106, 2008; Cell 131: p. 861-872, 2007; Science, 318: p. 1917-1920, 2007; Cell Stem Cells 1: p. 55-70, 2007; Nat Biotechnol, 25: p. 1177-1181, 2007; Nature, 448: p. 318-324, 2007; Cell Stem Cells 2: p. 10-12, 2008; Nature 451: p. 141-146, 2008; Science, 318: p. 1917-1920, 2007). A stem cell established by cultivating an early embryo produced by nuclear transplantation of the nucleus of somatic cell is also preferable as a pluripotent stem cell (Nature, 385, 810 (1997); Science, 280, 1256 (1998); Nature Biotechnology, 17, 456 (1999); Nature, 394, 369 (1998); Nature Genetics, 22, 127 (1999); Proc. Natl. Acad. Sci. USA, 96, 14984 (1999)), Rideout III et al. (Nature Genetics, 24, 109 (2000)).

Examples of the multipotent stem cell include somatic stem cells such as mesenchymal stem cell, hematopoietic stem cell, neural stem cell, myeloid stem cell, germ stem cell and the like, and the like. The multipotent stem cell is preferably a mesenchymal stem cell. The mesenchymal stem cell means a stem cell capable of differentiation into all or some of osteoblast, chondroblast and adipoblast. Multipotent stem cells can be isolated from a living organism by a method known per se. For example, mesenchymal stem cells can be collected from mammalian bone marrow, adipose tissue, peripheral blood, cord blood and the like by a known conventional method. For example, human mesenchymal stem cells can be isolated by culture or passage of hematopoietic stem cells after bone marrow aspiration and the like (Journal of Autoimmunity, 30 (2008) 163-171). Multipotent stem cells can also be obtained by cultivating the above-mentioned pluripotent stem cells under appropriate induction conditions.

The stem cells contained in the suspension of the present invention is preferably adhesive. This is because aggregation of adhesive stem cells, which easily occurs in a suspension, can be effectively suppressed, since the suspension of the present invention contains trehalose. In the present specification, the "adhesive" cell means an anchorage dependent cell which can survive, grow and produce substances by adhering to anchorage. Examples of the adhesive stem cell include pluripotent stem cell, mesenchymal stem cell, neural stem cell, myeloid stem cell, germ stem cell and the like. The adhesive stem cell is preferably a mesenchymal stem cell or a pluripotent stem cell.

The mammalian stem cells may be separated from the body or passage cultured in vitro.

The mammalian stem cells contained in the suspension of the present invention is preferably an isolated or purified cell. In the present specification, "isolated or purified" means that an operation to remove components other than the object component has been applied. The purity of the isolated or purified mammalian stem cells (proportion of the number of mammalian stem cells to the total number of cells) is generally not less than 30%, preferably not less than 50%, more preferably not less than 70%, still more preferably not less than 90% (for example, 100%).

The mammalian stem cells contained in the suspension of the present invention preferably contains mammalian stem cells in a single-cell state. In the present specification, the "single-cell state" means that the cell has not formed a mass together with other cells (i.e., no aggregation state). Mammalian stem cells in a single-cell state can be prepared by a treatment of mammalian stem cells cultured in vitro with an enzyme such as trypsin/EDTA etc. The population of mammalian stem cells in a single-cell state, which are contained in the mammalian stem cells, is generally not less than 70%, preferably not less than 90%, more preferably not less than 95%, still more preferably not less than 99% (for example, 100%).

The population of cells in a single-cell state can be determined by dispersing mammalian stem cells in PBS, observing them under a microscope, and examining the presence or absence of aggregation in randomly selected plural (e.g., 1000) cells.

In the suspension of the present invention, mammalian stem cells are preferably floating. In the present specification, "floating" means that the cells are maintained in a suspension without contacting the inner wall of the container containing the suspension.

The suspension of the present invention contains at least one polysaccharide selected from the group consisting of trehalose, hydroxyethylstarch and dextran. As shown in the below-mentioned Examples, the polysaccharides have an effect of suppressing aggregation of mammalian stem cells. Preferably, therefore, aggregation of mammalian stem cells is suppressed in the suspension of the present invention. In the present specification, "aggregation" refers to a phenomenon wherein two or more cells gather to form a mass.

Particularly, adhesive stem cells float in a suspension and easily aggregate when they are in a single-cell state. However, the above-mentioned polysaccharides effectively suppress aggregation, and a single-cell state can be maintained for a long time.

Although not bound by theory, when a stem cell suspension contains the above-mentioned polysaccharides, the floating state of the cells in the suspension is maintained comparatively for a long time, precipitation of the cells is suppressed, and the contact of the cells is suppressed. Furthermore, generally, when adherent cells are exposed to a floating state for a long time, the cells are stressed, and are known to form protrusion in an attempt to adhere to a dish and the like, depending on the floating time. However, since the above-mentioned polysaccharides (particularly trehalose) produce only a small stress on a cell, the formation of the protrusion is suppressed. Combined with such action, the above-mentioned polysaccharides are considered to afford a superior mammalian stem cell aggregation-suppressive effect.

As shown in the below-mentioned Examples, the above-mentioned polysaccharides have an effect of suppressing a decrease in the survival rate of mammalian stem cells. Preferably, therefore, a decrease in the survival rate of mammalian stem cells is suppressed in the suspension of the present invention. Particularly, adhesive stem cells are prone to suffer damage when they are floating in a suspension (especially, floating in a suspension and in a single-cell state), and the survival rate thereof easily decrease. However, by the addition of the above-mentioned polysaccharides, a decrease in the adhesive survival rate of the adhesive stem cells can be effectively suppressed.

The trehalose usable for the suspension of the present invention includes 3 kinds of α,α-trehalose, α,β-trehalose and β,β-trehalose. While the kind of trehalose is not particularly limited as long as it can suppress aggregation and/or a decrease in the survival rate of mammalian stem cells, α,α-trehalose is preferably used.

While the weight-average molecular weight (Mw) of hydroxyethylstarch usable for the suspension of the present invention is not particularly limited as long as it can suppress aggregation and/or a decrease in the survival rate of mammalian stem cells, it is generally within the range of $5\times10^4$-$67\times10^4$, preferably $7\times10^4$-$60\times10^4$, more preferably $7\times10^4$-$20\times10^4$.

To reinforce the suppressive effect on the aggregation and/or a decrease in the survival rate of mammalian stem cells of mammalian stem cells, hydroxyethylstarch having a comparatively low weight-average molecular weight (Mw) (e.g., $5\times10^4$-$9\times10^4$, preferably $6\times10^4$-$8\times10^4$ (e.g., $7\times10^4$)) is preferably used.

Also, while the degree of substitution (number of hydroxyethyl groups per 1 glucose unit) of hydroxyethylstarch usable for the suspension of the present invention is not particularly limited as long as it can suppress aggregation and/or a decrease in the survival rate of mammalian stem cells, it is generally 0.4-0.8.

Preferable examples of hydroxyethylstarch usable for the suspension of the present invention include hydroxyethylstarch having a weight-average molecular weight (Mw) of $7\times10^4$ and a degree of substitution of 0.50-0.55, and hydroxyethylstarch having a weight-average molecular weight (Mw) of $20\times10^4$ and a degree of substitution of 0.50-0.55 and the like. Such hydroxyethylstarch is commercially available from, for example, Fresenius Kabi Japan K.K. as HESPANDER (registered trade mark).

The dextran usable for the suspension of the present invention is a polysaccharide $(C_6H_{10}O_5)_n$, consisting of D-glucose, which has an α1→6 bond as a main chain. The kind of dextran is not particularly limited as long as it can suppress aggregation and/or a decrease in the survival rate of mammalian stem cells. The weight-average molecular weight (Mw) of dextran is not particularly limited as long as it can suppress aggregation and/or a decrease in the survival rate of mammalian stem cells. Dextran 40 (Mw=40000) and dextran 70 (Mw=70000) and the like are preferable examples.

The concentration of the above-mentioned polysaccharides in the suspension of the present invention is not particularly limited as long as it is sufficient to suppress aggregation and/or a decrease in the survival rate of mammalian stem cells. The higher the concentration of the above-mentioned polysaccharides is, the higher the effect of suppressing the aggregation and/or a decrease in the survival rate becomes. However, when the polysaccharides concentration is too high, the survival rate of the stem cells may be adversely influenced.

For example, when trehalose is used as the above-mentioned polysaccharide, the concentration of trehalose in the suspension of the present invention is generally not less than 4.53 mg/ml, preferably not less than 15.1 mg/ml. To avoid an adverse influence on the survival rate of the stem cells, the concentration of trehalose in the suspension is generally not more than 362.4 mg/ml, preferably not more than 181.2 mg/ml. Thus, the trehalose concentration of the suspension is generally 4.53-362.4 mg/ml, preferably 15.1-181.2 mg/ml.

Even when the above-mentioned polysaccharides other than trehalose are used, a concentration, which exhibits an effect of suppressing aggregation of stem cells and/or a decrease in the survival rate, and suppresses an adverse influence on the survival rate of the stem cells, can be appropriately determined according to the concentration of trehalose.

When hydroxyethylstarch is used as the above-mentioned polysaccharide, the concentration of hydroxyethylstarch in the suspension of the present invention is, for example, not less than 1 mg/ml, preferably not less than 10 mg/ml. In addition, to avoid an adverse influence on the survival rate of the stem cells, the concentration of hydroxyethylstarch in the suspension is, for example, not more than 500 mg/ml, preferably not more than 100 mg/ml. Thus, the concentration of hydroxyethylstarch in the suspension is, for example, 1-500 mg/ml, preferably 10-100 mg/ml.

When dextran is used as the above-mentioned polysaccharide, the concentration of dextran in the suspension of the present invention is, for example, not less than 1 mg/ml, preferably not less than 10 mg/ml, more preferably not less than 30 mg/ml, still more preferably not less than 65 mg/ml. In addition, to avoid an adverse influence on the survival rate of the stem cells, the concentration of dextran in the suspension is, for example, not more than 500 mg/ml, preferably not more than 200 mg/ml, more preferably not more than 125 mg/ml, still more preferably not more than 100 mg/ml. Thus, the concentration of dextran in the suspension is, for example, 1-500 mg/ml, preferably 10-200 mg/ml, more preferably 30-125 mg/ml, still more preferably 30-100 mg/ml, further more preferably 65-100 mg/ml.

The suspension of the present invention preferably comprises a combination of trehalose and hydroxyethylstarch, or trehalose and dextran. A combination of trehalose with hydroxyethylstarch or dextran is expected to enhance the effect of suppressing a decrease in the survival rate of the mammalian stem cells. Particularly, the combination is expected to effectively suppress a decrease in the survival rate of adhesive stem cells floating in the suspension (especially, adhesive stem cells floating in the suspension, and in a single-cell state).

When trehalose is used in combination with hydroxyethylstarch or dextran, the concentration of each polysaccharide in the suspension of the present invention is preferably set such that the effect of suppressing a decrease in the survival rate of the mammalian stem cells is enhanced more by using trehalose and hydroxyethylstarch or dextran in combination than by a single use of each of trehalose, hydroxyethylstarch and dextran.

In the suspension of the present invention, mammalian stem cells are suspended in an aqueous physiological solution containing at least one polysaccharide selected from the group consisting of trehalose, hydroxyethylstarch and dextran. The aqueous physiological solution is preferably an aqueous isotonic solution such as saline, phosphate buffered saline, tris buffered saline, HEPES buffered saline, Ringer's solution, 5% aqueous glucose solution, liquid medium for mammal culture, and aqueous solution of isotonic agent (glucose, D-sorbitol, D-mannitol, lactose, sodium chloride etc.), or the like. In the present specification, "isotonic" means that the osmotic pressure is within the range of 250-380 mOsm/l.

The aqueous physiological solution can further contain a stabilizer (e.g., human serum albumin, polyethylene glycol and the like), a buffering agent (e.g., phosphate buffer, sodium acetate buffer), a chelating agent (e.g., EDTA, EGTA, citric acid, salicylate), a solubilizing agent, a preservative, an antioxidant and the like.

The suspension of the present invention can be produced by suspending mammalian stem cells in an aqueous physiological solution containing at least one polysaccharide selected from the group consisting of trehalose, hydroxyethylstarch and dextran (preferably, aqueous isotonic solution containing at least one polysaccharide selected from the group consisting of trehalose, hydroxyethylstarch and dextran). The concentration of each polysaccharide in the aqueous physiological solution is the same as that of each polysaccharide in the above-mentioned suspension of the present invention. The present invention also provides such method of producing a mammalian stem cell suspension.

Suspending mammalian stem cells in an aqueous physiological solution containing the above-mentioned polysaccharides encompasses obtaining a mammalian stem cell suspension containing mammalian stem cells and the above-mentioned polysaccharides by adding the above-mentioned polysaccharides to the mammalian stem cell suspension.

Suspending mammalian stem cells in an aqueous physiological solution containing the above-mentioned polysaccharides can be performed by a method well known in the art such as pipetting, tapping and the like.

The temperature of the suspension of the present invention is within the range of generally 0-37° C., preferably 0-25° C.

The density of the mammalian stem cells in the suspension of the present invention is not particularly limited as long as the effect of suppressing aggregation and/or a decrease in the survival rate of mammalian stem cells by at least one polysaccharide selected from the group consisting of trehalose, hydroxyethylstarch and dextran can be achieved, and is generally within the range of $10^3$-$10^{10}$ cells/ml.

In a preferable embodiment, since aggregation of mammalian stem cells is suppressed by at least one polysaccharide selected from the group consisting of trehalose, hydroxyethylstarch and dextran in the suspension of the present invention, stem cell transplantation using the suspension can reduce the risk of stem cell aggregates plugging a cannula or forming emboli in thin blood vessels such as pulmonary vein and the like. In a preferable embodiment, moreover, since a decrease in the survival rate of the mammalian stem cells in the suspension is suppressed by at least one polysaccharide selected from the group consisting of trehalose, hydroxyethylstarch and dextran in the suspension of the present invention, stem cell transplantation can be performed in a better condition, and the treatment effect can be expected to be enhanced when using the suspension of the present invention. Thus, the present invention also provides a mammalian stem cell suspension preparation containing the above-mentioned suspension of the present invention.

The mammalian stem cell suspension preparation of the present invention can be produced by enclosing the above-mentioned suspension of the present invention in an appropriate sterilized container. Examples of the container include bottle, vial, syringe, plastic bag such as infusion bag and the like, test tube and the like. These containers can be formed from various materials such as glass or plastic. A cannula and/or an injection needle can be connected to these containers to enable drip infusion of the mammalian stem cell suspension in the container to the patients.

II. Suppression of Aggregation of Mammalian Stem Cells
(1. Mammalian Stem Cell Aggregation Inhibitor)

The present invention provides a mammalian stem cell aggregation inhibitor containing at least one polysaccharide selected from the group consisting of trehalose, hydroxyethylstarch and dextran. These polysaccharides particularly suppress aggregation of mammalian stem cells in a suspension (i.e., floating mammalian stem cells).

The definition of each term such as "trehalose", "hydroxyethylstarch", "dextran", "mammal", "stem cell", "adhesive", "isolated or purified", "single-cell state", "floating", "aggregation", "isotonic", "aqueous physiological solution", and the like is, unless otherwise specified, as described in the above-mentioned I.

The mammalian stem cells to be the application target of the aggregation inhibitor of the present invention are preferably adhesive stem cells. This is because adhesive stem cells in a suspension (i.e., in a floating state) more easily aggregate. The adhesive stem cells are preferably mesenchymal stem cells or pluripotent stem cells.

The mammalian stem cells may be separated from the body or passage cultured in vitro.

The mammalian stem cells to be the application target of the aggregation inhibitor of the present invention are preferably isolated or purified.

The mammalian stem cells to be the application target of the aggregation inhibitor of the present invention preferably contain mammalian stem cells in a single-cell state. The proportion of the mammalian stem cells in a single-cell state, which are contained in the mammalian stem cells, is generally not less than 70%, preferably not less than 90%, more preferably not less than 95%, still more preferably not less than 99% (for example, 100%).

The mammalian stem cells to be the application target of the aggregation inhibitor of the present invention are preferably floating in a suspension of the stem cells.

Particularly, adhesive stem cells float in a suspension and easily aggregate when they are in a single-cell state. However, the aggregation inhibitor of the present invention can effectively suppress aggregation, and a single-cell state can be maintained for a long time.

The aggregation inhibitor of the present invention comprises 1, 2 or 3 kinds of polysaccharides selected from the group consisting of trehalose, hydroxyethylstarch and dextran. When the aggregation inhibitor of the present invention contains 2 or 3 kinds of polysaccharides selected from these groups, the combination thereof is that of trehalose and hydroxyethylstarch, or trehalose and dextran, or hydroxyethylstarch and dextran, or trehalose and hydroxyethylstarch and dextran.

The aggregation inhibitor of the present invention may be at least one polysaccharide selected from the group consisting of trehalose, hydroxyethylstarch and dextran, or may further contain a physiologically acceptable carrier. Examples of the physiologically acceptable carrier include aqueous physiological solution (e.g., aqueous isotonic solutions such as saline, phosphate buffered saline, tris buffered saline, HEPES buffered saline, Ringer's solution, 5% aqueous glucose solution, liquid medium for mammalian culture, aqueous solution of isotonic agent (glucose, D-sorbitol, D-mannitol, lactose, sodium chloride etc.) and the like), stabilizer (e.g., human serum albumin, polyethylene glycol and the like), buffering agent (e.g., phosphate buffer, sodium acetate buffer), chelating agent (e.g., EDTA, EGTA, citric acid, salicylate), excipient, binder, solubilizing agents, preservative, antioxidant and the like. The aggregation inhibitor of the present invention is preferably an aqueous physiological solution containing at least one polysaccharide selected from the group consisting of trehalose, hydroxyethylstarch and dextran (solution of the above-mentioned polysaccharides in an aqueous physiological solution), more preferably an aqueous isotonic solution containing at least one polysaccharide selected from the group consisting of trehalose, hydroxyethylstarch and dextran.

The aggregation inhibitor of the present invention can be used by adding to a mammalian stem cell suspension. Alternatively, when the aggregation inhibitor of the present invention is an aqueous physiological solution containing at least one polysaccharide selected from the group consisting of trehalose, hydroxyethylstarch and dextran, the mammalian stem cells may be suspended in the aggregation inhibitor of the present invention. The aggregation inhibitor of the present invention is added, or mammalian stem cells are suspended in the aggregation inhibitor of the present invention, such that the concentration of the polysaccharides, which is sufficient to suppress the aggregation of mammalian stem cells, is achieved.

When trehalose is used as the above-mentioned polysaccharide, the trehalose concentration sufficient to suppress the aggregation of mammalian stem cells in the suspension is generally not less than 4.53 mg/ml, preferably not less than 15.1 mg/ml. The higher the trehalose concentration is, the higher the effect of suppressing the aggregation becomes. However, when the trehalose concentration is too high, the survival rate of the stem cells may be adversely influenced. To avoid an adverse influence on the survival rate of the stem cells, therefore, the concentration of trehalose in the suspension is generally not more than 362.4 mg/ml, preferably not more than 181.2 mg/ml. Thus, the trehalose concentration of the suspension is generally 4.53-362.4 mg/ml, preferably 15.1-181.2 mg/ml.

Even when the above-mentioned polysaccharides other than trehalose are used, a concentration sufficient to suppress the aggregation of mammalian stem cells in the suspension can be appropriately determined according to the concentration of trehalose.

When hydroxyethylstarch is used as the above-mentioned polysaccharide, the hydroxyethylstarch concentration sufficient to suppress the aggregation of mammalian stem cells in the suspension is, for example, not less than 1 mg/ml, preferably not less than 10 mg/ml. In addition, to avoid an adverse influence on the survival rate of the stem cells, the concentration of hydroxyethylstarch in the suspension is, for example, not more than 500 mg/ml, preferably not more than 100 mg/ml. Thus, the concentration of hydroxyethylstarch in the suspension is, for example, 1-500 mg/ml, preferably 10-100 mg/ml.

When dextran is used as the above-mentioned polysaccharide, the dextran concentration sufficient to suppress the aggregation of mammalian stem cells in the suspension is, for example, not less than 1 mg/ml, preferably not less than 10 mg/ml, more preferably not less than 30 mg/ml, still more preferably not less than 65 mg/ml. In addition, to avoid an adverse influence on the survival rate of the stem cells, the concentration of dextran in the suspension is, for example, not more than 500 mg/ml, preferably not more than 200 mg/ml, more preferably not more than 125 mg/ml, still more preferably not more than 100 mg/ml. Thus, the concentration of dextran in the suspension is, for example, 1-500 mg/ml, preferably 10-200 mg/ml, more preferably 30-125 mg/ml, still more preferably 30-100 mg/ml, further more preferably 65-100 mg/ml.

Moreover, when 2 or 3 kinds of polysaccharides selected from the group consisting of trehalose, hydroxyethylstarch and dextran are used, the aggregation inhibitor of the present invention is added, or mammalian stem cells are suspended in the aggregation inhibitor of the present invention, such that the aggregation of the mammalian stem cells in a suspension is consequently suppressed.

The aggregation inhibitor of the present invention contains at least one polysaccharide selected from the group consisting of trehalose, hydroxyethylstarch and dextran in an amount sufficient to suppress aggregation of mammalian stem cells when used as mentioned above. The content of the polysaccharides in the aggregation inhibitor of the present invention is generally within the range of 0.001-100 (w/w) %.

When the aggregation inhibitor of the present invention is an aqueous physiological solution containing at least one polysaccharide selected from the group consisting of trehalose, hydroxyethylstarch and dextran, the concentration of the polysaccharides in the aqueous solution is not particularly limited as long as it is sufficient to suppress aggregation of the mammalian stem cells. The higher the concentration of the above-mentioned polysaccharides is, the higher the effect of suppressing the aggregation becomes. However, when the polysaccharides concentration is too high, the survival rate of the stem cells may be adversely influenced.

For example, when trehalose is used as the above-mentioned polysaccharide, the concentration of trehalose in the aqueous solution is generally not less than 4.53 mg/ml, preferably not less than 15.1 mg/ml. To avoid an adverse influence on the survival rate of the stem cells, the concentration of trehalose in the aqueous solution is generally not more than 362.4 mg/ml, preferably not more than 181.2 mg/ml. Thus, the trehalose concentration of the aqueous solution is generally 4.53-362.4 mg/ml, preferably 15.1-181.2 mg/ml.

Even when the above-mentioned polysaccharides other than trehalose are used, a trehalose concentration sufficient to suppress aggregation of mammalian stem cells can be appropriately determined according to the concentration of trehalose.

When hydroxyethylstarch is used as the above-mentioned polysaccharide, the concentration of hydroxyethylstarch in the aqueous solution is, for example, not less than 1 mg/ml, preferably not less than 10 mg/ml. In addition, to avoid an adverse influence on the survival rate of the stem cells, the concentration of hydroxyethylstarch in the aqueous solution is, for example, not more than 500 mg/ml, preferably not more than 100 mg/ml. Thus, the concentration of hydroxyethylstarch in the aqueous solution is, for example, 1-500 mg/ml, preferably 10-100 mg/ml.

When dextran is used as the above-mentioned polysaccharide, the concentration of dextran in the aqueous solution of the present invention is, for example, not less than 1 mg/ml, preferably not less than 10 mg/ml, more preferably not less than 30 mg/ml, still more preferably not less than 65 mg/ml. In addition, to avoid an adverse influence on the survival rate of the stem cells, the concentration of dextran in the aqueous solution is, for example, not more than 500 mg/ml, preferably not more than 200 mg/ml, more preferably not more than 125 mg/ml, still more preferably not more than 100 mg/ml. Thus, the concentration of dextran in the aqueous solution is, for example, 1-500 mg/ml, preferably 10-200 mg/ml, more preferably 30-125 mg/ml, still more preferably 30-100 mg/ml, further more preferably 65-100 mg/ml.

Moreover, when 2 or 3 kinds of polysaccharides selected from the group consisting of trehalose, hydroxyethylstarch and dextran are used, the aqueous solution contains each polysaccharide, such that the aggregation of the mammalian stem cells is consequently suppressed.

By suspending mammalian stem cells in an aqueous physiological solution containing at least one polysaccharide selected from the group consisting of trehalose, hydroxyethylstarch and dextran, which has been prepared to such concentration, the aggregation of mammalian stem cells can be conveniently suppressed.

(2. Method of Suppressing Aggregation of Mammalian Stem Cells)

The present invention provides a method of suppressing aggregation of mammalian stem cells, comprising suspending mammalian stem cells in an aqueous physiological solution containing at least one polysaccharide selected from the group consisting of trehalose, hydroxyethylstarch and dextran (preferably, aqueous isotonic solution containing at least one polysaccharide selected from the group consisting of trehalose, hydroxyethylstarch and dextran). These polysaccharides particularly suppress aggregation of mammalian stem cells in a suspension (i.e., floating mammalian stem cells).

Suspending mammalian stem cells in an aqueous physiological solution containing at least one polysaccharide selected from the group consisting of trehalose, hydroxyethylstarch and dextran encompasses adding at least one polysaccharide selected from the group consisting of trehalose, hydroxyethylstarch and dextran to a mammalian stem cell suspension to give a mammalian stem cell suspension in the aqueous physiological solution containing the polysaccharides.

The definition of each term such as "trehalose", "hydroxyethylstarch", "dextran", "mammal", "stem cell", "adhesive", "isolated or purified", "single-cell state", "floating", "aggregation", "isotonic", "aqueous physiological solution", and the like is, unless otherwise specified, as described in the above-mentioned I.

The mammalian stem cells to be used for the method of suppressing aggregation of the present invention are preferably adhesive stem cells. This is because adhesive stem cells in a suspension (i.e., in a floating state) more easily aggregate. The adhesive stem cells are preferably mesenchymal stem cells or pluripotent stem cells.

The mammalian stem cells may be separated from the body or passage cultured in vitro.

The mammalian stem cells to be used for the aggregation suppressive method of the present invention are preferably isolated or purified.

The mammalian stem cells to be used for the method of suppressing aggregation of the present invention preferably contain mammalian stem cells in a single-cell state. The proportion of the mammalian stem cells in a single-cell state, which are contained in the mammalian stem cells, is generally not less than 70%, preferably not less than 90%, more preferably not less than 95%, still more preferably not less than 99% (for example, 100%).

Particularly, adhesive stem cells float in a suspension and easily aggregate when they are in a single-cell state. However, at least one polysaccharide selected from the group consisting of trehalose, hydroxyethylstarch and dextran can effectively suppress aggregation, and a single-cell state can be maintained for a long time.

The aqueous physiological solution to be used in the present invention contains 1, 2 or 3 kinds of polysaccharides selected from the group consisting of trehalose, hydroxyethylstarch and dextran. When the aqueous physiological solution contains 2 or 3 kinds of polysaccharides selected from these groups, the combination thereof is that of trehalose and hydroxyethylstarch, or trehalose and dextran, or hydroxyethylstarch and dextran, or trehalose, hydroxyethylstarch and dextran.

The aqueous physiological solution to be used in the present invention contains the above-mentioned polysaccharides at a concentration sufficient to suppress aggregation of mammalian stem cells.

When trehalose is used as the above-mentioned polysaccharide, the concentration of trehalose in the aqueous physiological solution is not particularly limited as long as it is sufficient to suppress aggregation of mammalian stem cells. It is generally not less than 4.53 mg/ml, preferably not less than 15.1 mg/ml. To avoid an adverse influence on the survival rate of the stem cells, the concentration of trehalose in the aqueous physiological solution is preferably not more than 362.4 mg/ml, more preferably not more than 181.2 mg/ml. Thus, the trehalose concentration of the aqueous physiological solution is preferably 4.53-362.4 mg/ml, more preferably 15.1-181.2 mg/ml.

Even when the above-mentioned polysaccharides other than trehalose are used, a concentration sufficient to suppress aggregation of mammalian stem cells can be appropriately determined according to trehalose.

When hydroxyethylstarch is used as the above-mentioned polysaccharide, the concentration of hydroxyethylstarch in the aqueous physiological solution is not particularly limited as long as it is sufficient to suppress aggregation of mammalian stem cells. It is, for example, not less than 1 mg/ml, preferably not less than 10 mg/ml. In addition, to avoid an adverse influence on the survival rate of the stem cells, the concentration of hydroxyethylstarch in the aqueous physiological solution is, for example, not more than 500 mg/ml, preferably not more than 100 mg/ml. Thus, the concentration of hydroxyethylstarch in the aqueous physiological solution is, for example, 1-500 mg/ml, preferably 10-100 mg/ml.

When dextran is used as the above-mentioned polysaccharide, the concentration of dextran in the aqueous physiological solution is not particularly limited as long as it is sufficient to suppress aggregation of mammalian stem cells. It is, for example, not less than 1 mg/ml, preferably not less than 10 mg/ml, more preferably not less than 30 mg/ml, still more preferably not less than 65 mg/ml. In addition, to avoid an adverse influence on the survival rate of the stem cells, the concentration of dextran in the aqueous physiological solution is generally not more than 500 mg/ml, preferably not more than 200 mg/ml, more preferably not more than 125 mg/ml, still more preferably not more than 100 mg/ml. Thus, the concentration of dextran in the aqueous physiological solution is generally 1-500 mg/ml, preferably 10-200 mg/ml, more preferably 30-125 mg/ml, still more preferably 30-100 mg/ml, further more preferably 65-100 mg/ml.

Moreover, when 2 or 3 kinds of polysaccharides selected from the group consisting of trehalose, hydroxyethylstarch and dextran are used, the aqueous physiological solution contains each polysaccharide, so that the aggregation of the mammalian stem cells can be consequently suppressed.

The temperature of an aqueous physiological solution containing at least one polysaccharide selected from the group consisting of trehalose, hydroxyethylstarch and dextran, when suspending mammalian stem cells, is within the range of generally 0-37° C., preferably 0-25° C.

The density of the mammalian stem cells in the suspension is not particularly limited as long as the aggregation suppressive effect of at least one polysaccharide selected from the group consisting of trehalose, hydroxyethylstarch and dextran can be achieved, and is generally within the range of $10^3$-$10^{10}$ cells/ml.

Suspending mammalian stem cells in an aqueous physiological solution containing at least one polysaccharide selected from the group consisting of trehalose, hydroxyethylstarch and dextran can be performed by a method well known in the technical field such as pipetting, tapping and the like. By such operation, mammalian stem cells float in an aqueous physiological solution containing at least one polysaccharide selected from the group consisting of trehalose, hydroxyethylstarch and dextran.

III. Suppression of Decrease in the Survival Rate of Mammalian Stem Cells (1. Inhibitor of Decrease in Survival Rate of Mammalian Stem Cells)

The present invention provides an inhibitor of a decrease in the survival rate of mammalian stem cells, which contains at least one polysaccharide selected from the group consisting of trehalose, hydroxyethylstarch and dextran. When the inhibitor of a decrease in the survival rate of mammalian stem cells contains 2 or 3 kinds of polysaccharides selected from these groups, a combination of trehalose and hydroxyethylstarch, a combination of trehalose and dextran, a combination of hydroxyethylstarch and dextran and a combination of trehalose and hydroxyethylstarch and dextran particularly suppress a decrease in the survival rate of mammalian stem cells in a suspension (i.e., floating mammalian stem cells).

The definition of each term such as "trehalose", "hydroxyethylstarch", "dextran", "mammal", "stem cell", "adhesive", "isolated or purified", "a single-cell state", "floating", "aggregation", "isotonic", "aqueous physiological solution", and the like is, unless otherwise specified, as described in the above-mentioned I.

The mammalian stem cells to be the application target of the inhibitor of a decrease in the survival rate of the present invention are preferably adhesive stem cells. This is because the survival rate of adhesive stem cells more easily decreases in a suspension (i.e., in a floating state) compared with nonadhesive cells. The adhesive stem cells are preferably mesenchymal stem cells or pluripotent stem cells.

The mammalian stem cells may be separated from the body or passage cultured in vitro.

The mammalian stem cells to be the application target of the inhibitor of a decrease in the survival rate of the present invention are preferably isolated or purified.

The mammalian stem cells to be used for the inhibitor of a decrease in the survival rate of the present invention preferably contain mammalian stem cells in a single-cell state.

The ratio of the mammalian stem cells in a single-cell state, which are contained in the mammalian stem cells, is generally not less than 70%, preferably not less than 90%, more preferably not less than 95%, still more preferably not less than 99% (for example, 100%).

The mammalian stem cells to be the application target of the inhibitor of a decrease in the survival rate of the present invention are preferably floating in a suspension of the stem cells.

Particularly, adhesive stem cells are prone to suffer damage when they are floating in a suspension and in a single-cell state, and the survival rate thereof easily decrease. However, a decrease in the survival rate of the adhesive stem cells can be effectively suppressed by the inhibitor of a decrease in the survival rate of the present invention.

The inhibitor of a decrease in the survival rate of the present invention preferably comprises a combination of trehalose and hydroxyethylstarch, or trehalose and dextran. A combination of trehalose with hydroxyethylstarch or dextran is expected to enhance the effect of suppressing a decrease in the survival rate of the mammalian stem cells. Particularly, the combination can be expected to effectively suppress a decrease in the survival rate of adhesive stem cells in the suspension in the state of floating (especially, adhesive stem cells in the state of floating in a suspension and in the state of single-cell).

The inhibitor of a decrease in the survival rate of the present invention may consist of at least one polysaccharide selected from the group consisting of trehalose, hydroxyethylstarch and dextran, or may further comprise a physiologically acceptable carrier in addition to these components. Examples of the physiologically acceptable carrier include aqueous physiological solution (e.g., aqueous isotonic solutions such as saline, phosphate buffered saline, tris buffered saline, HEPES buffered saline, Ringer's solution, 5% aqueous glucose solution, liquid medium for mammalian culture, aqueous solution of isotonic agent (glucose, D-sorbitol, D-mannitol, lactose, sodium chloride etc.) and the like), stabilizer (e.g., human serum albumin, polyethylene glycol and the like), buffering agent (e.g., phosphate buffer, sodium acetate buffer), chelating agent (e.g., EDTA, EGTA, citric acid, salicylate), excipient, binder, solubilizing agents, preservative, antioxidant and the like. The inhibitor of a decrease in the survival rate of the present invention is preferably an aqueous physiological solution containing 1, 2 or 3 kinds of polysaccharides selected from the group consisting of trehalose, hydroxyethylstarch and dextran (solution of the above-mentioned polysaccharides in an aqueous physiological solution), more preferably an aqueous isotonic solution containing 1, 2 or 3 kinds of polysaccharides selected from the group consisting of trehalose, hydroxyethylstarch and dextran.

The inhibitor of a decrease in the survival rate of the present invention can be used by adding to a mammalian stem cell suspension. Alternatively, when the inhibitor of a decrease in the survival rate of the present invention is an aqueous physiological solution containing at least one polysaccharide selected from the group consisting of trehalose, hydroxyethylstarch and dextran, the mammalian stem cells may be suspended in the inhibitor of a decrease in the survival rate of the present invention. The inhibitor of a decrease in the survival rate of the present invention is added, or mammalian stem cells are suspended in the inhibitor of a decrease in the survival rate of the present invention, such that the concentration of the above-mentioned polysaccharides sufficient to suppress a decrease in the survival rate of mammalian stem cells is achieved.

When trehalose is used as polysaccharide, the trehalose concentration sufficient to suppress a decrease in the survival rate of mammalian stem cells in the suspension is generally not less than 4.53 mg/ml, preferably not less than 15.1 mg/ml. The higher the concentration of trehalose is, the higher the effect of suppressing a decrease in the survival rate becomes. However, when the trehalose concentration is too high, conversely, the survival rate of the stem cells may be adversely influenced. Therefore, to avoid the adverse influence, the concentration of trehalose in the suspension is generally not more than 362.4 mg/ml, preferably not more than 181.2 mg/ml. Thus, the trehalose concentration of the suspension is generally 4.53-362.4 mg/ml, preferably 15.1-181.2 mg/ml.

Even when the above-mentioned polysaccharides other than trehalose are used, a trehalose concentration sufficient to suppress a decrease in the survival rate of the mammalian stem cells in a suspension can be appropriately determined according to trehalose.

When hydroxyethylstarch is used as polysaccharide, the concentration of hydroxyethylstarch sufficient to suppress a decrease in the survival rate of mammalian stem cells in the suspension is generally not less than 1 mg/ml, preferably not less than 10 mg/ml. The higher the concentration of hydroxyethylstarch is, the higher the effect of suppressing a decrease in the survival rate becomes. However, when the hydroxyethylstarch concentration is too high, conversely, the survival rate of the stem cells may be adversely influenced. Therefore, to avoid the adverse influence, the concentration of hydroxyethylstarch in the suspension is generally not more than 500 mg/ml, preferably not more than 100 mg/ml. Thus, the hydroxyethylstarch concentration of the suspension is generally 1-500 mg/ml, preferably 10-100 mg/ml.

When dextran is used as polysaccharide, the concentration of dextran sufficient to suppress a decrease in the survival rate of mammalian stem cells in the suspension is generally not less than 1 mg/ml, preferably, not less than 10 mg/ml, more preferably not less than 30 mg/ml, still preferably not less than 65 mg/ml. The higher the concentration of dextran is, the higher the effect of suppressing a decrease in the survival rate becomes. However, when the dextran concentration is too high, conversely, the survival rate of the stem cells may be adversely influenced. Therefore, to avoid the adverse influence, the concentration of dextran in the suspension is generally not more than 500 mg/ml, preferably not more than 200 mg/ml, more preferably not more than 125 mg/ml, still more preferably not more than 100 mg/ml. Thus, the dextran concentration of the suspension is generally 1-500 mg/ml, preferably 10-200 mg/ml, more preferably 30-125 mg/ml, still more preferably 30-100 mg/ml, further more preferably 65-100 mg/ml.

When a combination comprising trehalose and hydroxyethylstarch; trehalose and dextran; or trehalose, hydroxyethylstarch and dextran is used as polysaccharides, the concentration of each polysaccharide in the suspension is preferably set such that the effect of suppressing a decrease in the survival rate of the mammalian stem cells is enhanced more by using these combinations than by a single use of each of trehalose, hydroxyethylstarch and dextran.

The inhibitor of a decrease in the survival rate of the present invention contains at least one polysaccharide selected from the group consisting of trehalose, hydroxyethylstarch and dextran in an amount sufficient to suppress a decrease in the survival rate of mammalian stem cells when used as mentioned above. The content of the polysaccharides in the inhibitor of a decrease in the survival rate of the present invention is generally within the range of 0.001-100 (w/w) %.

When a combination comprising trehalose and hydroxyethylstarch, or trehalose and dextran is used as polysaccharide, the content of trehalose is within the range of generally 0.001-99.999 (w/w) %, and the content of hydroxyethylstarch or dextran is within the range of generally 0.001-99.999 (w/w) %, in the inhibitor of a decrease in the survival rate of the present invention.

When a combination comprising trehalose, hydroxyethylstarch and dextran is used as polysaccharide, the content of each polysaccharide in the inhibitor of a decrease in the survival rate of the present invention is within the range of generally 0.001-99.997 (w/w) %.

When the inhibitor of a decrease in the survival rate of the present invention is an aqueous physiological solution containing at least one polysaccharide selected from the group consisting of trehalose, hydroxyethylstarch and dextran, the concentration of the polysaccharides in the aqueous solution is not particularly limited as long as it is sufficient to suppress a decrease in the survival rate of the mammalian stem cells. The higher the concentration of the above-mentioned polysaccharides is, the higher the effect of suppressing a decrease in the survival rate becomes. However, when the polysaccharides concentration is too high, the survival rate of the stem cells may be adversely influenced.

For example, when trehalose is used as polysaccharide, the concentration of trehalose in the aqueous solution is generally not less than 4.53 mg/ml, preferably not less than 15.1 mg/ml, so that it is sufficient to suppress a decrease in the survival rate of mammalian stem cells. To avoid an adverse influence, moreover, the concentration of trehalose in the aqueous solution is generally not more than 362.4 mg/ml, preferably not more than 181.2 mg/ml. Thus, the trehalose concentration of the aqueous solution is generally 4.53-362.4 mg/ml, preferably 15.1-181.2 mg/ml.

Even when the above-mentioned polysaccharides other than trehalose are used, a concentration sufficient to suppress a decrease in the survival rate of the mammalian stem cells in a suspension can be appropriately determined according to the concentration of trehalose.

When hydroxyethylstarch is used as the above-mentioned polysaccharide, the concentration of hydroxyethylstarch in the aqueous solution is, for example, not less than 1 mg/ml, preferably not less than 10 mg/ml. In addition, to avoid an adverse influence, the concentration of hydroxyethylstarch in the aqueous solution is, for example, not more than 500 mg/ml, preferably not more than 100 mg/ml. Thus, the concentration of hydroxyethylstarch in the aqueous solution is, for example, 1-500 mg/ml, preferably 10-100 mg/ml.

When dextran is used as the above-mentioned polysaccharide, the concentration of dextran in the aqueous solution of the present invention is, for example, not less than 1 mg/ml, preferably not less than 10 mg/ml, more preferably not less than 30 mg/ml, still more preferably not less than 65 mg/ml. In addition, to avoid an adverse influence, the concentration of dextran in the aqueous solution is, for example, not more than 500 mg/ml, preferably not more than 200 mg/ml, more preferably not more than 125 mg/ml, still more preferably not more than 100 mg/ml. Thus, the concentration of dextran in the aqueous solution is, for example, 1-500 mg/ml, preferably 10-200 mg/ml, more preferably 30-125 mg/ml, still more preferably 30-100 mg/ml, further more preferably 65-100 mg/ml.

When a combination comprising trehalose and hydroxyethylstarch; trehalose and dextran; or trehalose, hydroxyethylstarch and dextran is used as polysaccharides, the concentration of each polysaccharide in the aqueous solution is preferably set such that the effect of suppressing a decrease in the survival rate of the mammalian stem cells is enhanced more by using these combinations than by a single use of each of trehalose, hydroxyethylstarch and dextran.

By suspending mammalian stem cells in an aqueous physiological solution containing at least one polysaccharide selected from the group consisting of trehalose, hydroxyethylstarch and dextran, which has been adjusted to such concentration, a decrease in the survival rate of the mammalian stem cells can be conveniently suppressed.

(2. Method of Suppressing Decrease in the Survival Rate of Mammalian Stem Cells)

The present invention provides a method of suppressing a decrease in the survival rate of mammalian stem cells, comprising suspending mammalian stem cells in an aqueous physiological solution containing 1, 2 or 3 kinds of polysaccharides selected from the group consisting of trehalose, hydroxyethylstarch and dextran (preferably, aqueous isotonic solution containing 1, 2 or 3 kinds of polysaccharides selected from the group consisting of trehalose, hydroxyethylstarch and dextran). When 2 or 3 kinds of polysaccharides are used in combination, a combination of trehalose and hydroxyethylstarch, a combination of trehalose and dextran, a combination of hydroxyethylstarch and dextran and a combination of trehalose, hydroxyethylstarch and dextran particularly suppress a decrease in the survival rate of mammalian stem cells in a suspension (i.e., floating mammalian stem cells).

Suspending mammalian stem cells in an aqueous physiological solution containing at least one polysaccharide selected from the group consisting of trehalose, hydroxyethylstarch and dextran also encompasses adding at least one polysaccharide selected from the group consisting of trehalose, hydroxyethylstarch and dextran to a mammalian stem cell suspension to give a suspension of mammalian stem cells in an aqueous physiological solution containing at least one polysaccharide selected from the group consisting of trehalose, hydroxyethylstarch and dextran.

The definition of each term such as "trehalose", "hydroxyethylstarch", "dextran", "mammal", "stem cell", "adhesive", "isolated or purified", "a single-cell state", "floating", "aggregation", "isotonic", "aqueous physiological solution", and the like is, unless otherwise specified, as described in the above-mentioned I.

The mammalian stem cells to be used for the method of suppressing a decrease in the survival rate of the present invention are preferably adhesive stem cells. This is because the survival rate of adhesive stem cells more easily decreases in a suspension (i.e., in a floating state) compared with nonadhesive cells. The adhesive stem cells are preferably mesenchymal stem cells or pluripotent stem cells.

The mammalian stem cells may be separated from the body or passage cultured in vitro.

The mammalian stem cells to be used for the method of suppressing a decrease in the survival rate of the present invention are preferably isolated or purified.

The mammalian stem cells to be used for the method of suppressing a decrease in the survival rate of the present invention preferably contain mammalian stem cells in a single-cell state. The proportion of the mammalian stem cells in a single-cell state, which are contained in the mammalian stem cells, is generally not less than 70%, preferably not less than 90%, more preferably not less than 95%, still more preferably not less than 99% (for example, 100%).

Particularly, adhesive stem cells are prone to suffer damage when they are floating in a suspension and in a single-cell state, and the survival rate thereof easily decrease. However, a decrease in the adhesive survival rate of the stem cells can be effectively suppressed by at least one polysaccharide selected from the group consisting of trehalose, hydroxyethylstarch and dextran.

The aqueous physiological solution to be used in the present invention preferably comprises a combination of trehalose and hydroxyethylstarch, or trehalose and dextran. A combination of trehalose with hydroxyethylstarch or dextran is expected to enhance the effect of suppressing a decrease in the survival rate of the mammalian stem cells. Particularly, the combination can be expected to effectively suppress a decrease in the survival rate of adhesive stem cells in the suspension in the state of floating (especially, adhesive stem cells in the state of floating in a suspension and in a single-cell state).

The concentration of the polysaccharides in an aqueous physiological solution containing at least one polysaccharide selected from the group consisting of trehalose, hydroxyethylstarch and dextran is not particularly limited as long as it is sufficient to suppress a decrease in the survival rate of mammalian stem cells.

For example, when trehalose is used as the above-mentioned polysaccharide, the concentration of trehalose in the aqueous solution is generally not less than 4.53 mg/ml, preferably not less than 15.1 mg/ml, so that it will be sufficient to suppress a decrease in the survival rate of mammalian stem cells. To avoid an adverse influence on the survival rate of the stem cells, the concentration of trehalose in the aqueous solution is generally not more than 362.4 mg/ml, preferably not more than 181.2 mg/ml. Thus, the trehalose concentration of the aqueous solution is generally 4.53-362.4 mg/ml, preferably 15.1-181.2 mg/ml.

Even when the above-mentioned polysaccharides other than trehalose are used, a concentration sufficient to suppress a decrease in the survival rate of the mammalian stem cells in a suspension can be appropriately determined according to trehalose.

When hydroxyethylstarch is used as the above-mentioned polysaccharide, the concentration of hydroxyethylstarch in the aqueous solution is, for example, not less than 1 mg/ml, preferably not less than 10 mg/ml. In addition, to avoid an adverse influence on the survival rate of the stem cells, the concentration of hydroxyethylstarch in the aqueous solution is, for example, not more than 500 mg/ml, preferably not more than 100 mg/ml. Thus, the concentration of hydroxyethylstarch in the aqueous solution is, for example, 1-500 mg/ml, preferably 10-100 mg/ml.

When dextran is used as the above-mentioned polysaccharide, the concentration of dextran in the aqueous solution of the present invention is, for example, not less than 1 mg/ml, preferably not less than 10 mg/ml, more preferably not less than 30 mg/ml, still more preferably not less than 65 mg/ml. In addition, to avoid an adverse influence on the survival rate of the stem cells, the concentration of dextran in the aqueous solution is, for example, not more than 500 mg/ml, preferably not more than 200 mg/ml, more preferably not more than 125 mg/ml, still more preferably not more than 100 mg/ml. Thus, the concentration of dextran in the aqueous solution is, for example, 1-500 mg/ml, preferably 10-200 mg/ml, more preferably 30-125 mg/ml, still more preferably 30-100 mg/ml, further more preferably 65-100 mg/ml.

When a combination comprising trehalose and hydroxyethylstarch; trehalose and dextran; or trehalose, hydroxyethylstarch and dextran is used as polysaccharides, the concentration of each polysaccharide in the aqueous solution is preferably set such that the effect of suppressing a decrease in the survival rate of the mammalian stem cells is enhanced more by using these combinations than by a single use of each of trehalose, hydroxyethylstarch and dextran.

The temperature of an aqueous physiological solution containing at least one polysaccharide selected from the group consisting of trehalose, hydroxyethylstarch and dextran, when suspending mammalian stem cells, is within the range of generally 0° C.-37° C., preferably 0° C.-25° C.

The density of the mammalian stem cells in the suspension is not particularly limited as long as the aggregation suppressive effect of trehalose is achieved, and is generally within the range of $10^3$-$10^{10}$ cells/ml.

Suspending mammalian stem cells in an aqueous physiological solution containing at least one polysaccharide selected from the group consisting of trehalose, hydroxyethylstarch and dextran can be performed by a method well known in the art such as pipetting, tapping and the like. By such operation, mammalian stem cells float in an aqueous physiological solution containing at least one polysaccharide selected from the group consisting of trehalose, hydroxyethylstarch and dextran.

All references cited in the present specification, including publication, patent document and the like, are hereby incorporated individually and specifically by reference, to the extent that the entireties thereof have been specifically disclosed herein.

While the present invention is more specifically explained in the following by referring to Examples, it is not limited in any way by the Examples shown below.

EXAMPLES

Example 1

1. Preparation of Swine Subcutaneous Adipose Tissue-Derived Mesenchymal Stem Cells (Pig AT-MSCs)
(1) Preparation of Swine Tissue Swine subcutaneous adipose tissues were collected from the inguinal region, visible tissues different from adipose tissues such as blood vessel, muscle and the like were removed with micro scissors, and thereafter, mincing and washing with HBSS (Hanks' solution) were repeated several times. Washing was continued until removal of blood cells (or clots) and removal of membranous floating substances such as muscle and the like could be visually confirmed. The obtained swine subcutaneous adipose tissues were minced with scissors.

The minced tissues were mixed with the same amount of HBSS. The mixture was gently shaken and left standing to allow separation into 2 layers. Only the upper layer was recovered. 0.2% Collagenase (Type I)/HBSS was added to the recovered upper layer and the mixture was gently shaken at 37° C. until the adipose tissues completely became liquid (maximum 90 min). To the reaction mixture was added 10% fetal bovine serum (FBS)-containing αMEM in an amount equivalent to or more than the amount of the collagenase reaction mixture. After mixing, the mixture was separated into 3 layers (nucleated cell, solution and fat, from the bottom) by centrifugation. Only the lower layer was recovered and resuspended in HBSS. This operation was repeated three times. Finally, the cell suspension in αMEM containing 10% FBS was transferred to a culture dish and cultured. MSCs adhered to the bottom of the culture dish.
(2) Preparation of Cells (Pig AT-MSCs P6) to be Used in the Experiment In the operation of (1), MSCs that adhered to the culture dish continued to grow and, 5-7 days later, the bottom of the culture dish was densely filled with the cells. Upon reaching confluence, discontinuation of growth or cell death is induced in MSCs. Before reaching confluence, therefore, MSCs were detached from the culture dish and plated on a fresh culture dish at a low density. MSCs that adhered to the bottom of the culture dish were washed three times with PBS, and trypsin-EDTA (0.25% trypsin, 1 mM EDTA·4Na) was added. MSCs were detached from the culture dish, suspended in 10% FBS-containing αMEM in an amount that affords low density of the cells, and transferred to a fresh culture dish. This operation was repeated 6 times (6 passages=P6).
(3) Suspending Cells in Each Solution The Pig AT-MSCs P6 obtained in (2) were used for the experiment.

The cells were washed three times with 5 ml PBS(−) per 10 cm dish, and detached by treating with 1 ml trypsin-EDTA (0.25% trypsin, 1 mM EDTA·4Na) for 20 sec into a single-cell state. The obtained cells were transferred into a 15 ml FALCON tube and recovered by centrifugation. After washing twice with PBS(−), the cells were subjected to be washed once again with each solution [ET-kyoto (ET-K, manufactured by Otsuka Pharmaceutical Factory, Inc.), HBSS, MSCM (DMEM+10% FBS)] for adaptation. ET-K contains trehalose at a concentration of 45.3 mg/ml. Thereafter, the cells were suspended in each solution to $2.5 \times 10^5$ cells/50 μL.

The suspension was left standing at each temperature (0, 25, and 37° C.), pipetted several times with 20 μL PIPETMAN 0, 30, 60, 120 and 240 min later, and 10 μL thereof was transferred to a dish.

A stereomicroscope was focused on the lowermost surface of the suspension on the dish, and observation was performed.

The cells forming a mass with adjacent cells under the microscope were taken as cell aggregate mass. The cell aggregate mass was confirmed to be obviously moving as a mass by shaking the dish on the stage of the microscope.

2. Examination of Cell Survival Rate

An influence of each condition on the cell survival rate was examined.

The number of the surviving cells per 50 µL was calculated by Trypan Blue staining, and the survival rate of the cells was calculated by comparing the number with that of the surviving cells in 50 µL at the time of the start ($2.5 \times 10^5$ cells). The results are shown in Table 1.

TABLE 1

Survival rate of MSCs in various cell suspensions

|  | 0 | 25 | 37 |
|---|---|---|---|
| 30 min ||||
| MSCM | 88.3 | 90 | 90.2 |
| HBSS | 82.5 | 91.4 | 93.3 |
| ETK | 97.2 | 95 | 93.8 |
| 60 min ||||
| MSCM | 84.4 | 83.9 | 82 |
| HBSS | 85.7 | 79.2 | 88.1 |
| ETK | 89.8 | 86 | 84.8 |
| 120 min ||||
| MSCM | 78.5 | 82.3 | 75.4 |
| HBSS | 79 | 80.4 | 77.8 |
| ETK | 86.8 | 84.7 | 82.1 |
| 240 min ||||
| MSCM | 83.1 | 74.5 | 55.6 |
| HBSS | 79 | 84.4 | 59.5 |
| ETK | 84.5 | 78.7 | 72.5 |

When MSCM or HBSS was used, the cell survival rate markedly decreased with the progress of time. However, a decrease in the survival rate was suppressed with ET-K.

3. Examination of Cell Aggregation State

When MSCM was used, formation of cell aggregate masses was observed from 30 min after the start of the test at 25° C. and 37° C. Even at 0° C., formation of cell aggregate masses was also observed from 60 min after the start of the test.

When HBSS was used, formation of cell aggregate masses was observed from 120 min after the start of the test at 25° C. and 37° C. Even at 0° C., formation of cell aggregate masses was also observed after 240 min from the start of the test.

On the other hand, when ET-K was used, formation of a cell aggregate masses was not observed until after 120 min from the start of the test at 25° C. and 37° C., and formation of cell aggregate masses was somewhat observed after 240 min from the start of the test. At 0° C., formation of cell aggregate masses was not observed even after 240 min from the start of the test. When ET-K was used, the floating state of the cells was maintained until 240 min from the start of the test at any temperature.

4. Examination of Cell Morphology

When MSCM was used, some of the cells were observed to have formed protrusion. The appearance rate of swollen cells was low.

When HBSS was used, the proportion of the cells with protrusion increased over time. In addition, the appearance rate of swollen cells was high.

On the other hand, when ET-K was used, the proportion of the cells with protrusion was low as compared to MSCM and HBSS. The appearance rate of swollen cells was low as compared to MSCM and HBSS.

Generally, adherent cells are known to form protrusion in an attempt to adhere to a dish and the like depending on the floating time. This is because the floating state applies a stress to the cells. In addition, swelling of the cell is considered to indicate decreased osmotic-pressure control potency inside and outside the cytoplasm. From the above observation results of the cell morphology, ET-K was considered to pose a minor stress on the cells as compared to other composition solutions.

Example 2

The swine subcutaneous adipose tissue-derived mesenchymal stem cells prepared in Example 1 were passaged twice and the obtained cells (Pig AT-MSCs P2) were plated on three 10 cm-dishes. The cells were washed three times with 5 ml PBS(−) per 10 cm dish, and detached by treating with 1 ml trypsin-EDTA (0.25% trypsin, 1 mM EDTA·4Na) for 20 sec into a single-cell state. The obtained cells ($1.7 \times 10^6$ cells; survival rate, 94.1%) were transferred into a 15 ml FALCON tube, recovered by centrifugation, washed twice with PBS(−), and suspended in 5 mL of ET-kyoto (ET-K manufactured by Otsuka Pharmaceutical Factory, Inc.). The cell suspension in ET-K was dispensed by 500 µL to ten 15 mL tubes, and left standing at room temperature (25° C.) for 10 min. An appropriate amount of saline was added to each tube to dilute the cell suspension in ET-K 2- to 10-fold and the mixture was further left standing for 30 min. Thereafter, in the same manner as in Example 1, the survival rate was calculated and the presence or absence of the cell aggregate mass was observed. The results are shown in Table 2.

TABLE 2

| dilution rate | 1 | 2 | 3 | 4 | 5 | 6 | 7 | 8 | 9 | 10 |
|---|---|---|---|---|---|---|---|---|---|---|
| cell number | 1.25 | 1 | 1.25 | 0.92 | 1 | 1 | 1.25 | 0.92 | 1 | 0.92 |
| survival rate | 91.5 | 92.3 | 90.2 | 92.3 | 82.3 | 88.3 | 93.1 | 90.1 | 90.5 | 83.5 |
| aggregate number | 0 | 0 | 0 | 2 | 2 | 2-3 | 2 | 2-3 | 2-3 | 2-3 |
| aggregation ratio | 0 | 0 | 0 | 1 or less | 1 or less | 1 or less | 1 or less | 1 or less | 1 or less | 1 or less |
| total liquid volume | 0.5 | 1 | 1.5 | 2 | 2.5 | 3 | 3.5 | 4 | 4.5 | 5 |
| trehalose concentration (mg/ml) | 45.3 | 22.65 | 15.1 | 11.33 | 9.06 | 7.55 | 6.47 | 5.66 | 5.03 | 4.53 |

(Cell Aggregability)

When a stock solution of ET-K, a 2-fold diluted solution thereof and a 3-fold diluted solution thereof were used, a cell aggregate mass was not observed. When ET-K was diluted 4-fold or more, aggregate masses of 2-3 bonded cells were slightly observed. Therefore, it was suggested that a stem cell aggregation suppressive effect is exhibited at a trehalose concentration of at least not less than 15.1 mg/ml.

(Cell Floating Property)

After observation of cell aggregability, the cells were resuspended, left standing at room temperature (25° C.) for 10 min, and the cell floating property was observed under a microscope. When ET-K stock solution, a 2-fold diluted solution thereof and a 3-fold diluted solution thereof were used, the cells floated stably. On the other hand, when ET-K was diluted 8-fold or more, the cells precipitated mostly in the same manner as with MSCM and HBSS. Therefore, it was suggested that the stem cells float stably at a trehalose concentration of at least 15.1 mg/ml or more.

(Cell Morphology and Survival Rate)

Even when ET-K was diluted with saline, no significant change in the cell morphology or survival rate was observed within the tested range of the dilution rate.

Example 3

The swine subcutaneous adipose tissue-derived mesenchymal stem cells prepared in Example 1 were passaged ten times and the obtained cells (Pig AT-MSCs P10) were plated on 10-cm dishes. The cells were washed three times with 5-ml PBS(−) per 10-cm dish, and detached by treating with 1-ml trypsin-EDTA (0.25% trypsin, 1 mM EDTA·4Na) for 20 sec into a single-cell state. The obtained cells ($3.3 \times 10^8$ cells; survival rate, 98.5%) were transferred to a 15-ml FALCON tube, recovered by centrifugation, washed twice with PBS(−), and suspended in 5 mL of ET-kyoto (ET-K manufactured by Otsuka Pharmaceutical Factory, Inc.). The cell suspension in ET-K was left standing at 4° C. for 5 hr or 27 hr. Thereafter, in the same manner as in Example 1, the survival rate was calculated and the presence or absence of a cell aggregate mass was observed. The results are shown in Table 2. After standing for 5 hr or 27 hr, the cells were further cultured for 24 hr, after which the cell morphology was observed under a microscope.

(Cell Aggregability)

After being detached from the dish, the cells were suspended in ET-K and left standing at 4° C. As a result, cell aggregation did not occur at any time point of 5 hr and 27 hr later, and a single-cell state was maintained. Thus, it was shown that a cell aggregation suppressive effect provided by ET-K is exhibited even at 4° C.

(Survival Rate)

The survival rate at 5 hr later was 78.7%, and that at 27 hr later was 65.9%. The survival rate was observed to decrease by 3.96%/hr from 0 hr to 5 hr and by 0.58%/hr from 5 hr to 27 hr.

(Cell Morphology)

After standing for 5 hr or 27 hr, the cells were further cultivated for 24 hr. As a result, the cells that adhered to the plate were observed to be consistent with the survival rate. However, about 10% of the cells preserved for 27 hr were observed to have irregular morphology. The proportion of the cells with irregular morphology was not more than 1% of the cells preserved for 5 hr.

Example 4

(1) Preparation of Human Bone Marrow Derived MSCs (hBM-MSCs)

Bone marrow cells (20-30 mL) were collected from human iliac bone with a syringe containing 6000 unit heparin. The bone marrow cells were washed once with PBS(−), and recovered by centrifugation at 900 g for 20 min, which was repeated again. The cells were suspended in αMEM containing 10% FBS, transferred to a culture dish and adhesion culture was performed.

(2) Preparation of Cells (hBM-MSCs P3) to be Used for the Experiment

By the operation of (1), MSCs that adhered to the culture dish continued to grow and, 5-7 days later, the bottom of the culture dish was densely filled with the cells. Upon reaching confluence, discontinuation of growth or cell death is induced in MSC. Before reaching confluence, therefore, MSC was detached from the culture dish and plated on a fresh culture dish at a low density. MSCs that adhered to the bottom of the culture dish was washed three times with PBS, and trypsin-EDTA (0.05% trypsin, 0.53 mM EDTA·4Na) was added. MSCs were detached from the culture dish, suspended in 10% FBS-containing αMEM in an amount that affords low density of the cells, and transferred to a fresh culture dish. This operation was repeated 3 times (3 passages=P3).

Human bone marrow cell-derived MSCs were plated on a 10-cm dish and cultured. The cells were washed three times with 5-ml PBS(−) per 10-cm dish, and detached by treating with 1-ml trypsin-EDTA (0.25% trypsin, 1 mM EDTA·4Na) for 20 sec into a single-cell state. The obtained cells were transferred into a 15-ml FALCON tube, recovered by centrifugation, washed twice with PBS(−), and suspended in the solutions with following composition. After standing for 240 min and 480 min, the presence or absence of the cell aggregation was observed.

NS: saline (Otsuka Pharmaceutical Factory, Inc.)
H: HESPANDER (KYORIN Pharmaceutical Co., Ltd.)
1×T&NS: saline containing 45.3 mg/mL D-(+)-trehalose (Wako Pure Chemical Industries, Ltd.)
1×T&H: HESPANDER (KYORIN Pharmaceutical Co., Ltd.) containing 45.3 mg/mL D-(+)-trehalose (Wako Pure Chemical Industries, Ltd.)
1×T&H&TRase: HESPANDER (KYORIN Pharmaceutical Co., Ltd.) containing 45.3 mg/mL D-(+)-trehalose (Wako Pure Chemical Industries, Ltd.) and 2 unit/mL trehalase (SIGMA).

Trehalose is a major component of ET-K, and 45.3 mg/mL is the concentration of trehalose contained in ET-K. HESPANDER is a hydroxyethylstarch preparation containing 6 (w/v) % of hydroxyethylstarch (weight-average molecular weight (Mw), about 70000; degree of substitution, 0.50-0.55).

As a result, when NS and H were used, formation of cell aggregate masses was observed after 240 min from the start of the test. On the other hand, when 1×T&NS and 1×T&H were used, formation of cell aggregate masses was not observed both at 240 min and 480 min from the start of the test. However, when trehalose was decomposed by trehalase, formation of a cell aggregate mass was observed.

From the above results, it was shown that the cell aggregation suppressive effect of ET-K is caused by trehalose.

Example 5

(1) Preparation of Human Adipose Tissue-Derived MSCs (hBM-MSCs)

Human subcutaneous adipose tissues were collected, visible tissues different from adipose tissues such as blood vessel, muscle and the like were removed with micro scissors, and thereafter, mincing and washing with HBSS (Hanks' solution) were repeated several times. Washing was continued until removal of blood cells (or clots) and removal of membranous floating substances such as muscle and the like could be visually confirmed. The obtained human subcutaneous adipose tissues were minced with scissors.

The minced tissues were mixed with the same amount of HBSS. The mixture was gently shaken and left standing to allow separation into 2 layers. Only the upper layer was recovered. 0.05% Collagenase (Type I)/HBSS was added to the recovered upper layer and the mixture was gently shaken at 37° C. until the adipose tissues completely became liquid. To the reaction mixture was added 10% fetal bovine serum (FBS)-containing αMEM. After mixing, the mixture was separated into 2 layers by centrifugation. Only the lower layer was recovered and resuspended in HBSS. This operation was repeated three times. Finally, the cell suspension in αMEM containing 10% FBS was transferred to a culture dish and cultured. MSCs adhered to the bottom of the culture dish.

(2) Preparation of Cells (hAT-MSCs P3) for Experiment

By the operation of (1), MSCs that adhered to the culture dish continued to grow and, 5-7 days later, the bottom of the culture dish was densely filled with the cells. Upon reaching confluence, discontinuation of growth or cell death is induced in MSC. Before reaching confluence, therefore, MSCs were detached from the culture dish and plated on a fresh culture dish at a low density. MSCs that adhered to the bottom of the culture dish was washed three times with PBS, and trypsin-EDTA (0.05% trypsin, 0.53 mM EDTA·4Na) was added. MSCs were detached from the culture dish, suspended in 10% FBS-containing αMEM in an amount that affords low density of the cells, and transferred to a fresh culture dish. This operation was repeated 3 times (3 passages=P3).

The cells obtained by passaging hAT-MSCs and hBM-MSCs three times (hAT-MSC P3 and hBM-MSC P3) were plated on 10-cm dishes. The cells were washed three times with 5-ml PBS(−) per 10-cm dish, and detached by treating with 1-ml trypsin-EDTA (0.25% trypsin, 1 mM EDTA·4Na) for 20 sec into a single-cell state. The obtained cells (hAT-MSCs P3, $1.0 \times 10^5$ cells: survival rate, 98.4%: hBM-MSCs P3, $1.25 \times 10^5$ cells; survival rate, 96.8%) were transferred to a 15-ml FALCON tube, recovered by centrifugation, washed twice with PBS(−), and suspended in the following composition solutions (100 µL). After standing at room temperature (about 25° C.) for 240 min or 24 hr, the survival rate of the cells was measured, and the cell aggregation and morphology were observed. Furthermore, after standing for 240 min or 24 hr, the cells were further cultured for 12 hr and the cell morphology was observed.

0.1×T&H: HESPANDER (KYORIN Pharmaceutical Co., Ltd.) containing 4.53 mg/mL D-(+)-trehalose (Wako Pure Chemical Industries, Ltd.)

0.1×T&NS: saline (Otsuka Pharmaceutical Factory, Inc.) containing 4.53 mg/mL D-(+)-trehalose 1×T&H: HESPANDER containing 45.3 mg/mL D-(+)-trehalose 1×T&NS: saline containing 45.3 mg/mL D-(+)-trehalose 2×T&H: HESPANDER containing 90.6 mg/mL D-(+)-trehalose 2×T&NS: saline containing 90.6 mg/mL D-(+)-trehalose ET-K: ET-Kyoto (Otsuka Pharmaceutical Factory, Inc.)

H: HESPANDER

NS: saline

MSCM: αMEM containing 10% FBS (Cell Survival Rate)

The results are shown in Table 3.

TABLE 3

| | AT | BM (%) |
|---|---|---|
| 240 min | | |
| 0.1 × T&H | 70 | 71.8 |
| 0.1 × T&NS | 61.5 | 50 |
| 1 × T&H | 75 | 77.8 |
| 1 × T&NS | 58.3 | 54.5 |
| 2 × T&H | 83.3 | 80 |
| 2 × T&NS | 64.3 | 45.5 |
| ET-K | 81.8 | 80 |
| H | 72.7 | 75 |
| NS | 58.3 | 40 |
| MSCM | 36.4 | 46.2 |
| 24 hr | | |
| 0.1 × T&H | 61.4 | 54.3 |
| 0.1 × T&NS | 50 | 46.2 |
| 1 × T&H | 66.7 | 64.3 |
| 1 × T&NS | 35.7 | 41.2 |
| 2 × T&H | 73.3 | 76.9 |
| 2 × T&NS | 27.3 | 33.3 |
| ET-K | 66.7 | 64.3 |
| H | 43.8 | 36.4 |
| NS | 21.4 | 27.3 |
| MSCM | 12.5 | 16.7 |

The cell survival rate increased by single addition of trehalose or hydroxyethylstarch (HESPANDER). The cell survival rate dramatically increased by the addition of both trehalose and hydroxyethylstarch (HESPANDER).

(Cell Aggregation and Morphology)

In 0.1×T&NS, formation of cell aggregate masses was slightly observed for both AT and BM 240 min after the start of the test. On the other hand, in other groups containing trehalose in the composition solution (0.1×T&H, 1×T&H, 1×T&NS, 2×T&H, 2×T&NS and ET-K), formation of a cell aggregate mass was not observed. In the groups containing trehalose in the composition solutions, deformation of the cell was not observed.

In the groups free of trehalose and hydroxyethylstarch in the composition solutions (NS, MSCM), cell aggregate masses and cell deformation were markedly observed. In the group containing only hydroxyethylstarch (H), cell aggregate masses were observed, but the cell deformation was small.

(Culture after Standing)

Regardless of addition or no addition of trehalose, increase and decrease in the number of adherent cells consistent with the survival rate were confirmed. In a part of the groups containing 0.1×T and the groups free of trehalose, abnormal cell morphology was confirmed. On the other hand, H showed good cell morphology compared with NS, and increase and decrease in the number of adherent cells according to the survival rate were observed.

From the above results, it was shown that trehalose can suppress cell aggregation, increase the survival rate of the cell, and maintain cell morphology and function. In addition, it was shown that hydroxyethylstarch can increase the survival rate of the cell, and maintain cell morphology and function. Furthermore, it was shown that a combination of trehalose and hydroxyethylstarch markedly increases the survival rate of the cell.

Example 6 hAT-MSCs and hBM-MSCs were passaged three times and the obtained cells (hAT-MSCs P3 and hBM-MSCs P3)

were plated on 10 cm-dishes. The cells were washed three times with 5-ml PBS(−) per 10-cm dish, and detached by treating with 1-ml trypsin-EDTA (0.25% trypsin, 1 mM EDTA·4Na) for 20 sec into a single-cell state. The obtained cells (hAT-MSCs P3, 4.25×10$^5$ cells; survival rate, 97.5%: hBM-MSCs P3, 5.0×10$^5$ cells; survival rate, 98.2%) were transferred to a 15-ml FALCON tube, recovered by centrifugation, washed twice with PBS(−), and suspended in the following composition solution (100 μL). After standing at room temperature (about 25° C.) for 8 hr or 36 hr, the survival rate of the cells was measured and the cell aggregation was observed.

1×T&H: HESPANDER (KYORIN Pharmaceutical Co., Ltd.) containing 45.3 mg/mL D-(+)-trehalose (Wako Pure Chemical Industries, Ltd.)
2×T&H: HESPANDER containing 90.6 mg/mL D-(+)-trehalose
4×T&H: HESPANDER containing 181.2 mg/mL D-(+)-trehalose
8×T&H: HESPANDER containing 362.4 mg/mL D-(+)-trehalose
ET-K: ET-Kyoto (Otsuka Pharmaceutical Factory, Inc.)
H: HESPANDER
1×T&H&TRase: HESPANDER containing 45.3 mg/mL D-(+)-trehalose and trehalase (SIGMA) (2 unit/mL)

(Cell Aggregation)

In the groups containing trehalose in the composition solutions (1×T&H, 2×T&H, 4×T&H, 8×T&H and ET-K), formation of cell aggregate masses was not observed for both hAT-MSCs and hBM-MSCs 8 hr after the start of the test. On the other hand, when HESPANDER (H), free of trehalose, was used, formation of a cell aggregate mass was observed for both hAT-MSCs and hBM-MSCs 8 hr after the start of the test. Furthermore, when trehalose was decomposed by trehalase, formation of cell aggregate masses was observed (1×T&H&TRase). From the above results, it was shown that trehalose has a cell-aggregation suppressive effect.

(Cell Survival Rate)

The cell survival rate 36 hr after the start of the test is shown in Table 4.

TABLE 4

|  | AT | BM |
| --- | --- | --- |
| 1 × T&H | 60 | 62.5 |
| 2 × T&H | 70 | 71.4 |
| 4 × T&H | 75.9 | 75 |
| 8 × T&H | 39.1 | 40.4 |
| H | 34.4 | 23.3 |
| 1 × T&H&TR | 28.6 | 22.6 |
| ET-K | 52.8 | 45.8 |

As shown in Table 4, the survival rate of the cell by adding any concentration of trehalose was higher than by adding HESPANDER (H) alone. While the cell survival rate markedly increased up to the addition of trehalose at a concentration of 181.2 mg/mL (4×T), the effect was attenuated conversely when the trehalose concentration was increased to 362.4 mg/mL (8×T). Therefore, to increase the cell survival rate, the trehalose concentration was suggested to be preferably not more than 181.2 mg/mL (4×T).

Example 7 hAT-MSCs and hBM-MSCs were passaged 6 or 8 times and the obtained cells (hAT-MSCs P8 and hBM-MSCs P6) were plated on 10 cm-dishes. The cells were washed three times with 5-ml HESPANDER (KYORIN Pharmaceutical Co., Ltd.) per 10-cm dish, and detached by treating with 1-ml trypsin-EDTA (0.25% trypsin, 1 mM EDTA·4Na) for 20 sec into a single-cell state. The obtained cells (hAT-MSCs P8, 2.4×10$^6$ cells; hBM-MSCs P6, 2.3×10$^6$ cells) were transferred to a 15-ml FALCON tube, recovered by centrifugation, and suspended in the following composition solution. After standing at room temperature (about 25° C.) for 1 hr, the survival rate of the cells was measured and the cell aggregation was observed.

Figure 2:
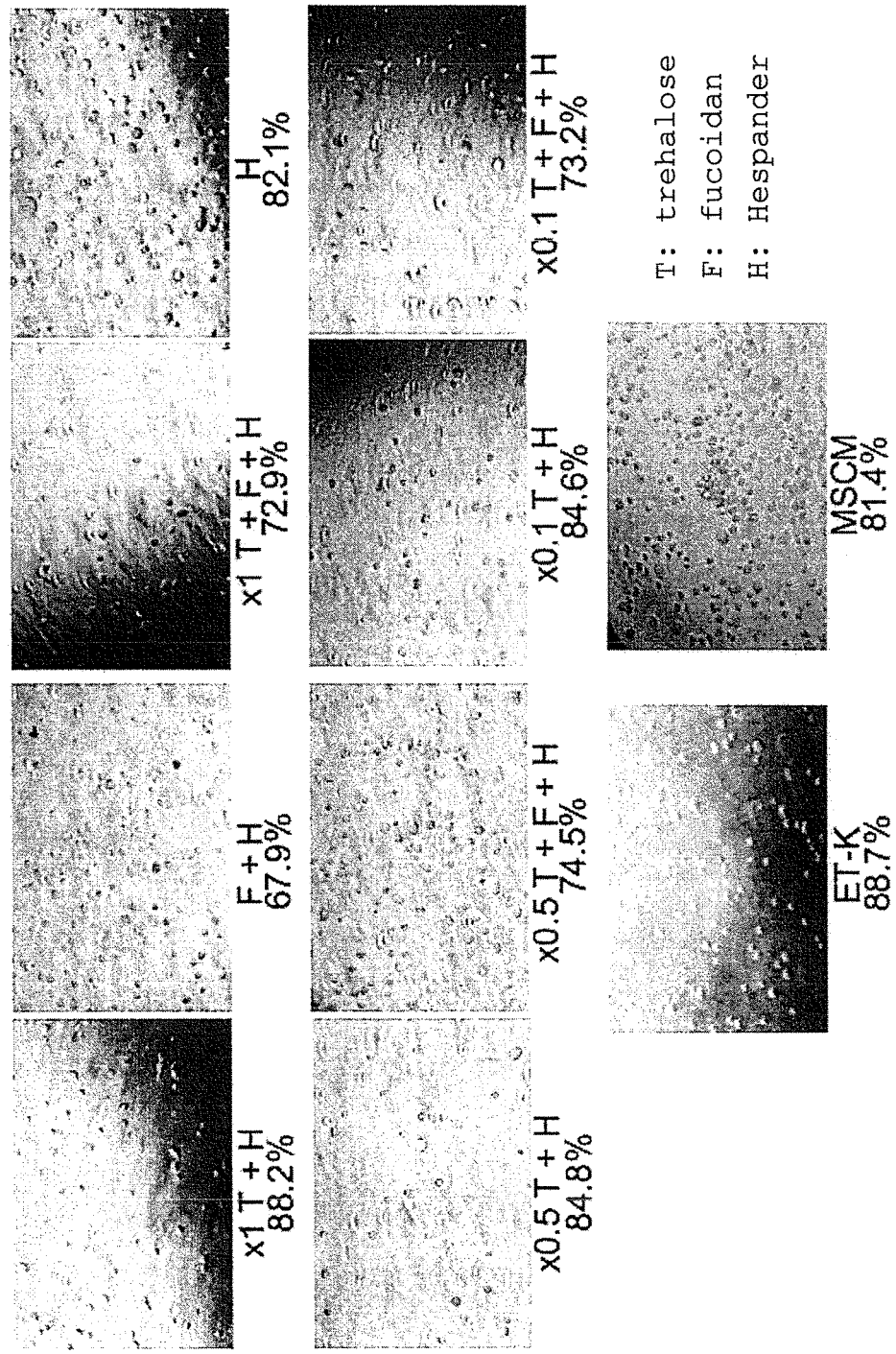
FIG. 2 shows the shape and survival rate of hAT-MSC P8 after standing in each composition solution at 25° C. for 1 hr.

1×T&H: HESPANDER containing 45.3 mg/mL D-(+)-trehalose (Wako Pure Chemical Industries, Ltd.)
0.5×T&H: HESPANDER containing 22.65 mg/mL D-(+)-trehalose
0.1×T&H: HESPANDER containing 4.53 mg/mL D-(+)-trehalose
1×T&F&H: HESPANDER containing 45.3 mg/mL D-(+)-trehalose and 10 μg/ml fucoidan (Yaizu Suisankagaku Industry)
0.5×T&F&H: HESPANDER containing 22.65 mg/mL D-(+)-trehalose and 10 μg/ml fucoidan
0.1×T&F&H: HESPANDER containing 4.53 mg/mL D-(+)-trehalose and 10 μg/ml fucoidan
F&H: HESPANDER containing 10 μg/ml fucoidan
ET-K: ET-Kyoto (Otsuka Pharmaceutical Factory, Inc.)
H: HESPANDER
MSCM: αMEM containing 10% FBS The test results are shown in FIGS. 1 and 2.

(Cell Survival Rate)

The survival rate of the cell by adding any concentration of trehalose was higher than by adding HESPANDER (H) alone. Since addition of fucoidan resulted in a decrease in the cell survival rate, fucoidan was suggested to have cytotoxicity. Trehalose showed a tendency to suppress the cytotoxicity of fucoidan.

(Cell Aggregation)

For both hAT-MSCs and hBM-MSCs, a cell floating effect and a cell aggregation suppressive effect were observed by the addition of trehalose. On the other hand, fucoidan showed a tendency to inhibit cell floating, and showed no cell-aggregation suppressive effect. Formation of protrusion from the cell was suppressed and the cell morphology was good when trehalose was added rather than adding HESPANDER alone. The cell-aggregation suppressive effect of 0.5×T&H was similar to that of ET-K. The cell floating effect of ET-K was slightly superior to that of 0.5×T&H. In 0.1×T&H, protrusion on the cell surface was slightly observed.

Example 8

The swine subcutaneous adipose tissue-derived mesenchymal stem cells prepared in Example 1 were passaged seven times and the obtained cells (Pig AT-MSCs P7) were cultured on 10-cm dishes. The cells were washed three times with 5-ml PBS(−) per 10-cm dish, detached by treating with 1-ml trypsin-EDTA (0.25% trypsin, 1 mM EDTA·4Na) for 20 sec into a single-cell state, and suspended in ET-K solution. The obtained cell suspension was used for the following test.

(Evaluation of Adhesiveness to the Inner Wall of Infusion Bag)

Soldem 3AG infusion bag (TERUMO) was finely cut and a piece thereof was placed on the wall of a 50-ml tube. The tube was filled with a cell suspension, laid down and left standing in a clean bench at room temperature (25° C.) for 30 min. Thereafter, the infusion bag piece was washed with PBS, and the presence or absence of cell adhesion to the inner wall of the infusion bag was evaluated by microscopic observation.

Before washing with PBS, a part of MSCs (estimated to be not more than 10%) was found to have adhered to the infusion bag inner wall. By washing with PBS, however, the adhered MSCs were mostly removed (estimated to be not less than 90%). Thus, the possibility of trehalose to avoid the cell adhesion to the inner wall of infusion bag was shown.

(Catheter Passage Test)

A CV catheter kit (Japan Sherwood Medical Industries Ltd.) was used. An 18G injection needle was connected to the tip of a catheter. A cell suspension was pulled into a 5-mL syringe. The syringe was set on the catheter and the cell suspension was pushed out. This operation was repeated the predetermined times, the cell survival rate was measured, and the cells were observed with a microscope. Before microscopic observation, the catheter was washed with 5-mL PBS.

The results are shown in Table 5.

TABLE 5

| number of catheter passage | 0 | 5 | 10 |
|---|---|---|---|
| cell number (×10$^5$) | 3.5 | 3.5 | 3.5 |
| survival rate (%) | 85.7 | 85.7 | 85.7 |

The cell survival rate did not change regardless of the number of passages at least up to 10 times. While slight MSCs and residual ET-K solution were observed on the inner wall of the catheter, the number of the cells after passage through catheter did not change, and adherent cells were not observed after washing with PBS. Therefore, the possibility of trehalose to avoid the cell adhesion to the catheter inner wall was shown.

Example 9

Swine mesenchymal stem cells were cultured on 10 cm-dishes. The cells were detached by treating with trypsin-EDTA (0.25% trypsin, 1 mM EDTA·4Na) in to a single-cell state. The obtained cells were suspended in the following composition solution and left standing at room temperature (about 25° C.) for 360 min. The survival rate of the cells was measured and the cell aggregation was observed.
NS: saline
MSCM: αMEM containing 10% FBS
ET-K: ET-Kyoto (Otsuka Pharmaceutical Factory, Inc.)
Saviosol: Saviosol (Otsuka Pharmaceutical Factory, Inc.)
Dextran: low molecular dextran L injection (Otsuka Pharmaceutical Factory, Inc.)

Saviosol is a lactated Ringer's solution containing dextran having a weight-average molecular weight of 40000 (dextran 40) at a concentration of 30 mg/ml. A low molecular dextran L injection is a lactated Ringer's solution containing dextran having a weight-average molecular weight of 40000 (dextran 40) at a concentration of 100 mg/ml.

(Cell Survival Rate)

The cell survival rates 30 min and 360 min after the start of the test are shown in Table 6.

TABLE 6

|  | 30 min | 360 min |
|---|---|---|
| NS | 8.3% | 0.0% |
| MSCM | 87.5% | 73.3% |
| ET-K | 83.3% | 70.6% |
| Saviosol | 93.3% | 62.5% |
| Dextran | 85.7% | 73.3% |

As shown in Table 6, the survival rates of the cells were markedly high, irrespective of the composition used compared with the use of saline.

(Cell Aggregation)

360 min after the start of the test, the presence or absence of cell aggregation was observed under a microscope. When the cells were preserved in saline or MSCM, formation of a large cell aggregate mass was observed; however, in ET-K, Saviosol and Dextran, formation of a cell aggregate mass was suppressed, and the dispersion state of the cell was maintained.

Example 10

(1) Preparation of Rat Tissue

Rat subcutaneous adipose tissues were collected from the inguinal region, visible tissues different from adipose tissues such as blood vessel, muscle and the like were removed with micro scissors, and thereafter, mincing and washing with HBSS (Hanks' solution) were repeated several times. Washing was continued until removal of blood cells (or clots) and removal of membranous floating substances such as muscle and the like could be visually confirmed. The obtained rat subcutaneous adipose tissues were minced with scissors.

The minced tissues were mixed with the same amount of HESS. The mixture was gently shaken and left standing to allow separation into 2 layers. Only the upper layer was recovered. 0.2% Collagenase (Type I)/HBSS was added to the recovered upper layer and the mixture was gently shaken at 37° C. until the adipose tissues completely became liquid (maximum 90 min). To the reaction mixture was added 10% fetal bovine serum (FBS)-containing αMEM in an amount equivalent to or more than the amount of the collagenase reaction mixture. After mixing, the mixture was separated into 3 layers (nucleated cell, solution and fat, from the bottom) by centrifugation. Only the lower layer was recovered and resuspended in HBSS. This operation was repeated three times. Finally, the cell suspension in αMEM containing 10% FBS was transferred to a culture dish and cultured. MSCs adhered to the bottom of the culture dish.

(2) Preparation of Cells (Rat AT-MSCs P6) to be Used for Experiment

In the operation of (1), MSCs that adhered to the culture dish continued to grow and, 5-7 days later, the bottom of the culture dish was densely filled with the cells. Upon reaching confluence, discontinuation of growth or cell death is induced in MSCs. Before reaching confluence, therefore, MSCs were detached from the culture dish and plated on a fresh culture dish at a low density. MSCs that adhered to the bottom of the culture dish were washed three times with PBS, and trypsin-EDTA (0.25% trypsin, 1 mM EDTA·4Na) was added. MSCs were detached from the culture dish, suspended in 10% FBS-containing αMEM in an amount that affords low density of the cells, and transferred to a fresh culture dish. This operation was repeated 6 times (6 passages=P6).

(3) Suspending cells in each solution

The Rat AT-MSCs P6 obtained in (2) was used for the experiment.

The cells were washed three times with 5-ml PBS(−) per 10-cm dish, and detached by treating with 1-ml trypsin-EDTA (0.25% trypsin, 1 mM EDTA·4Na) for 20 sec into a single-cell state. The obtained cells were transferred into a 15-ml FALCON tube and recovered by centrifugation. After washing twice with PBS(−), the cells were subjected to an acclimation-washing once again with each of the following solutions.

Saline: saline
Medium: αMEM containing 10% FBS
ET-K: ET-Kyoto (Otsuka Pharmaceutical Factory, Inc.)
Saviosol: Saviosol (Otsuka Pharmaceutical Factory, Inc.)
HES70K: 6 (w/v) % hydroxyethylstarch (weight-average molecular weight 70000)+0.9 (w/v) % NaCl (Braun GmbH, Germany)
HES200K: 6 (w/v) % hydroxyethylstarch (weight-average molecular weight 200000)+0.9 (w/v) % NaCl (Fresenius Kabi AG, Germany)
ET-K+Saviosol: mixture of ET-K and Saviosol (1:1 volume ratio)

Thereafter, the cells were suspended using each solution to $2.5 \times 10^5$ cells/50 μL.

The suspension was left standing at each temperature (0, 25, 37° C.), pipetted several times with 20 μL PIPETMAN 30-360 min later, and 10 μL was transferred to a dish.

A stereomicroscope was focused on the lowermost surface of the suspension on the dish, and observation was performed.

The cells forming masses with adjacent cells under the microscope were taken as cell aggregate mass. The cell aggregate mass was confirmed to be obviously moving as a mass by shaking the dish on the stage of the microscope.

(Cell Survival Rate)

Figure 3:
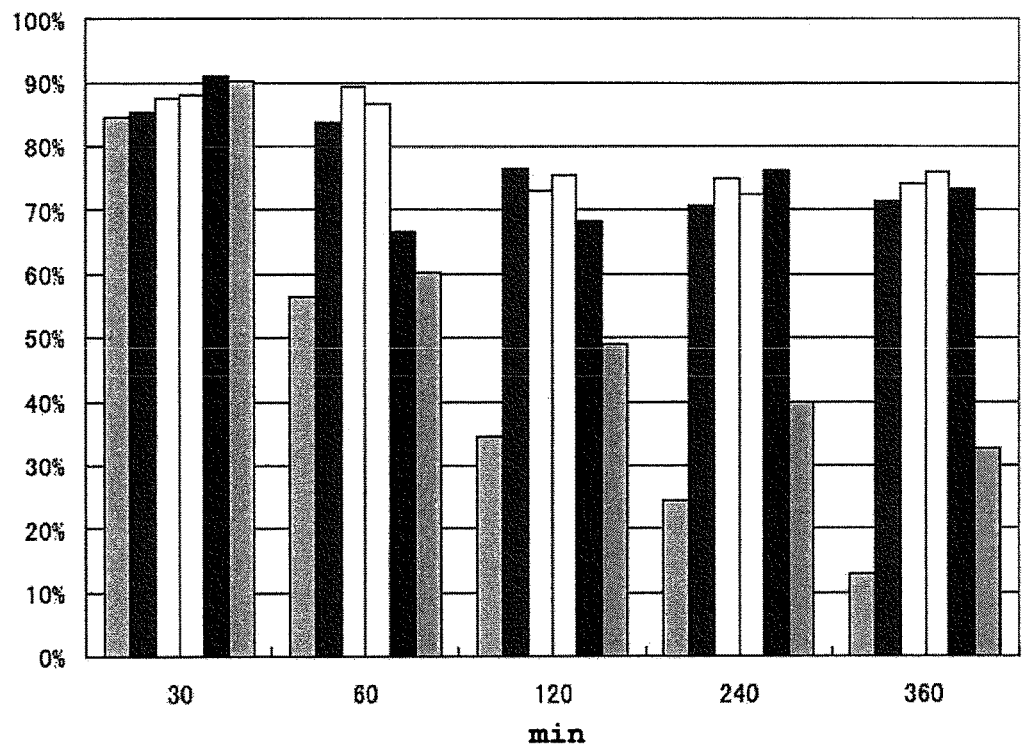
FIG. 3 shows the survival rates after standing in each composition solution at 25° C., wherein 6 bars show Saline, Medium, ET-K, Saviosol, HES70K and HES200K from the left.
Figure 4:
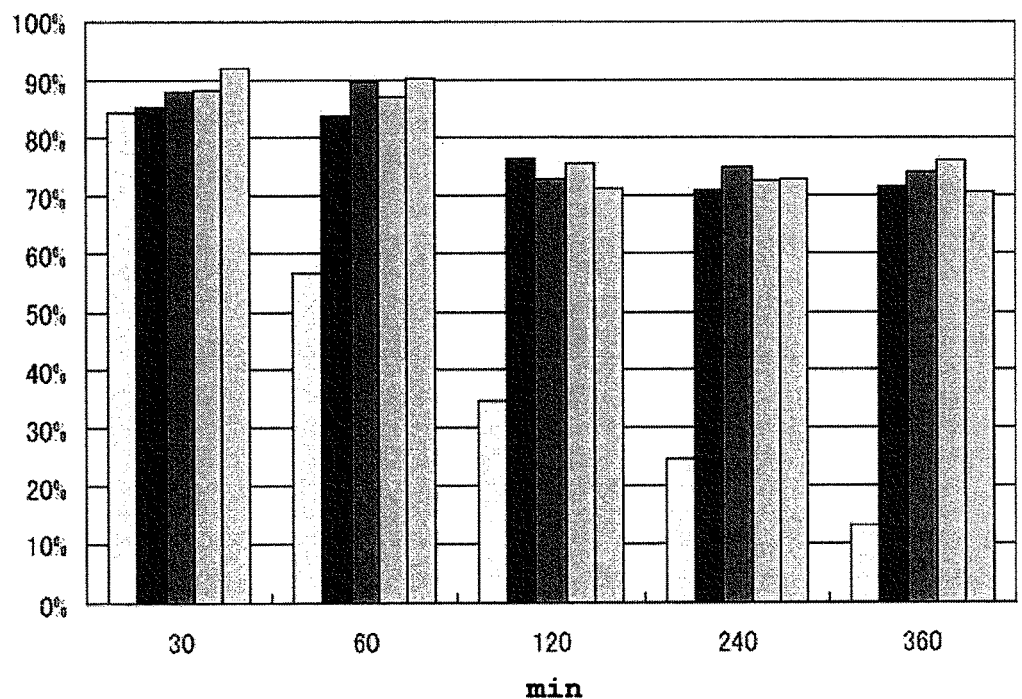
FIG. 4 shows the survival rates after standing in each composition solution at 25° C., wherein 5 bars show Saline, Medium, ET-K, Saviosol and ET-K+Saviosol from the left.

The cell survival rates 30-360 min after the start of the test are shown in FIGS. 3 and 4. As shown in these Figures, the survival rates of the cells were markedly high, irrespective of the composition used compared with the use of saline. The effect of suppressing a decrease in the survival rate of the cells was higher in HES70K than HES200K.

(Cell Aggregation)

The cell aggregavility was observed under a microscope 360 min after the start of the test. The results are shown in Table 7.

TABLE 7

| Aggregability | |
|---|---|
| saline | + |
| medium | +++ |
| ET-K | − |
| Saviosol | − |
| HES70K | − |
| HES200K | + |
| ET-K + Saviosol | − |

As compared with preservation in a medium, formation of a cell aggregate mass was suppressed under other conditions. The effect of suppressing cell aggregation was higher in HES70K than HES200K. In ET-K, Saviosol, HES70K and ET-K+Saviosol, formation of cell aggregation was not observed and the dispersion of the cell was well maintained.

Example 11

Each of the bone marrow-derived mesenchymal stem cells (passage number 8) and adipose tissue-derived mesenchymal stem cells (passage number 8), which were separated and purified from human, was cultured until they cover about 90% of the bottom of a culture dish manufactured by NUNC. The culture dish was washed three times with PBS(−) (manufactured by TaKaRa Bio, Inc.). Each mesenchymal stem cells were detached with a trypsin solution (manufactured by Gobco, US) from the culture dish and recovered in a 15 mL centrifugation tube manufactured by Assist. Cell aggregates were formed on the bottom of the centrifugation tube by a centrifugation operation at 1000 rpm for 5 min, and the supernatant was discarded by an aspirator. The cell aggregate was broken by tapping with a finger, and PBS(−) (manufactured by TaKaRa) was added. The cells were further broken by pipetting several times, and centrifuged at 1000 rpm for 5 min. Formation of cell aggregates on the bottom of the centrifugation tube was confirmed, and the supernatant was discarded by an aspirator. This washing operation with PBS(−) was repeated two more times. The number of the cells was measured with a hemocytometer, and the cells were transferred to a 1.5-mL tube manufactured by Assist under the condition of $1.0 \times 10^6$ cells/tube. Cell aggregates were formed on the bottom of the tube by a centrifugation operation at 1000 rpm for 5 min, and the supernatant was removed by a micropipette. To each tube was added each of total 4 kinds of solutions of (1) saline (manufactured by Otsuka Pharmaceutical Factory, Inc., 1 mL), (2) a mixture of Saviosol (manufactured by Otsuka Pharmaceutical Factory, Inc., 500 μL) and dextran L injection (manufactured by Otsuka Pharmaceutical Factory, Inc., 500 μL) (dextran 40 6.5 (w/v) %), (3) a mixture of Saviosol (manufactured by Otsuka Pharmaceutical Factory, Inc., 250 μL) and dextran L injection (manufactured by Otsuka Pharmaceutical Factory, Inc., 750 μL) (dextran 40 8.25 (w/v) %), and (4) dextran L injection (manufactured by Otsuka Pharmaceutical Factory, Inc., dextran 40 10 (w/v) %, 1 mL), and the mixtures were mixed with a vortex mixer for several seconds. Using a 30G injection needle and 1-mL syringe (manufactured by TERUMO Corporation), the cells were processed into a single-cell state, and left standing on a tube stand at room temperature (about 25° C.). After 30 min- and 60 min-standing, the solution (10 μL) was taken from each tube, mixed with an equal amount of a Trypan Blue solution manufactured by GIBCO and the solution was subjected to the measurement of the cell number and survival rate by a hemocytometer. The evaluated solutions were gently separated from three parts of each tube: the center of the liquid surface (top), the center of the middle of the liquid (middle) and the center of the bottom of the tube (low). With the total of the cell numbers of the upper, middle and low as 100%, the distribution state of the cells was calculated as the proportions of each cell number as the numerator and the total cell number as the denominator. In addition, the survival rate of the whole cells was separately calculated.

Figure 5:
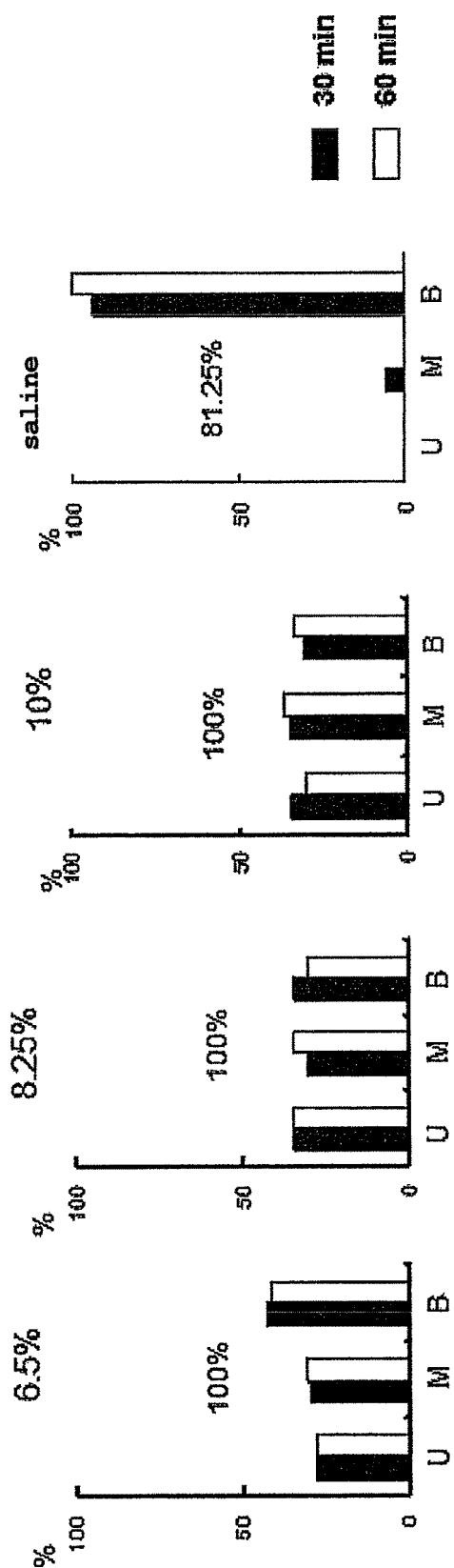
FIG. 5 shows the number of human bone marrow-derived mesenchymal stem cells in the upper, middle and lower layers of a tube when preserved in a buffer containing dextran 40 (6.5-10 (w/v) %) or saline, wherein the numerical value in the center of the graph shows the survival rate of the total cells.

The results are shown in FIGS. 5 and 6. When the mesenchymal stem cells were preserved in a dextran-containing buffer (6.5-10 (w/v) %), the numbers of the cells at the upper, middle and low of the tube did not show a great difference, regardless of the derivation of the mesenchymal stem cells, and the maintenance of uniform dispersion of the cells was shown. In this case, moreover, the survival rate of the cells remained the same and was 100%. On the other hand, when saline was used, the cells precipitated on the bottom of the tube, and the survival rate of the cells after preservation for 60 min decreased to 80%.

INDUSTRIAL APPLICABILITY

Using the present invention, aggregation of stem cells in a suspension can be suppressed during transplantation of the stem cells. As a result, the risk of stem cell aggregates plugging a cannula or forming emboli in thin blood vessels such as pulmonary vein and the like decreases.

Using the present invention, moreover, a decrease in the survival rate of the stem cells in a suspension can be suppressed. As a result, a treatment can be performed using stem cells in a better condition, and therefore, the treatment effect can be expected to be enhanced.

Therefore, the present invention is useful in the field of transplantation therapy utilizing stem cells.

This application is based on patent application No. 2010-251273 filed in Japan (filing date: Nov. 9, 2010) and patent application No. 2010-293908 (filing date: Dec. 28, 2010), the contents of which are incorporated in full herein.

The invention claimed is:

1. A method of suppressing aggregation of mammalian stem cells in a mammalian stem cell suspension, comprising suspending the mammalian stem cells in an aqueous physiological solution containing trehalose, and not containing serum albumin to prepare a mammalian stem cell suspension, wherein the mammalian stem cell suspension is suitable for transplantation into a body, and wherein the concentration of trehalose is 15.1-362.4 mg/ml.

2. The method of suppressing aggregation of mammalian stem cells according to claim 1, wherein the stem cells are adhesive stem cells.

3. The method of suppressing aggregation of mammalian stem cells according to claim 2, wherein the adhesive stem cells are mesenchymal stem cells or pluripotent stem cells.

4. The method of suppressing aggregation of mammalian stem cells according to claim 1, wherein the mammalian stem cells comprise mammalian stem cells in a single-cell state.

5. A method for suppressing cellular aggregation during transplantation comprising transplanting mammalian stem cells suspended in an aqueous physiological solution containing trehalose and not containing serum albumin, wherein the aqueous physiological solution contains trehalose in a concentration of at least 15.1-362.4 mg/ml mg/ml.

6. The method for suppressing cellular aggregation during transplantation according to claim 5, wherein the mammalian stem cells are adhesive stem cells.

7. The method for suppressing cellular aggregation during transplantation according to claim 6, wherein the adhesive stem cells are mesenchymal stem cells or pluripotent stem cells.

8. The method for suppressing cellular aggregation during transplantation according to claim 5, wherein the mammalian stem cells comprise mammalian stem cells in a single-cell state.

* * * * *

UNITED STATES PATENT AND TRADEMARK OFFICE
CERTIFICATE OF CORRECTION

PATENT NO. : 10,087,421 B2  
APPLICATION NO. : 13/883371  
DATED : October 2, 2018  
INVENTOR(S) : Eiji Kobayashi et al.

Page 1 of 1

It is certified that error appears in the above-identified patent and that said Letters Patent is hereby corrected as shown below:

In the Claims

At Column 36, Line 13 (Claim 5, Line 6) please change "concentration of at least 15.1 - 362.4 mg/ml mg/ml." to -- concentration of 15.1 - 362.4 mg/ml. --.

Signed and Sealed this  
Fifteenth Day of January, 2019

Andrei Iancu  
*Director of the United States Patent and Trademark Office*